US008575106B2

(12) United States Patent
Santhanam et al.

(10) Patent No.: US 8,575,106 B2
(45) Date of Patent: Nov. 5, 2013

(54) COSMETIC USES OF MODIFIED STRESSED YEAST EXTRACTS AND RELATED COMPOSITIONS

(75) Inventors: Uma Santhanam, Tenafly, NJ (US); Christos D. Kyrou, Goshen, NY (US); Desiree Mazich, Sparta, NJ (US); Qi Hong, Whippany, NJ (US); Hussam H. Shaheen, Lebanon, NH (US)

(73) Assignee: Avon Products, Inc., New York, NY (US)

( * ) Notice: Subject to any disclaimer, the term of this patent is extended or adjusted under 35 U.S.C. 154(b) by 182 days.

(21) Appl. No.: 12/850,193

(22) Filed: Aug. 4, 2010

(65) Prior Publication Data

US 2011/0052517 A1 Mar. 3, 2011

Related U.S. Application Data

(60) Provisional application No. 61/238,427, filed on Aug. 31, 2009.

(51) Int. Cl.
*A61K 38/00* (2006.01)
*A61P 17/00* (2006.01)
*A61P 29/00* (2006.01)
*A61K 8/00* (2006.01)
*A61K 8/18* (2006.01)
*A61Q 5/08* (2006.01)
*A61Q 19/02* (2006.01)

(52) U.S. Cl.
USPC .............................. 514/18.8; 424/62; 514/18.7

(58) Field of Classification Search
None
See application file for complete search history.

(56) References Cited

U.S. PATENT DOCUMENTS

| | | | |
|---|---|---|---|
| 2,239,345 A | 4/1941 | Sperti et al. | |
| 4,458,066 A | 7/1984 | Caruthers et al. | |
| 5,643,587 A | 7/1997 | Scancarella et al. | |
| 5,676,956 A | 10/1997 | Duffy et al. | |
| 5,776,441 A | 7/1998 | Scancarella et al. | |
| 6,461,857 B1 | 10/2002 | Scholz et al. | |
| 6,562,321 B2 * | 5/2003 | Ptchelintsev et al. | 424/62 |
| 6,858,212 B2 | 2/2005 | Scholz et al. | |
| 6,908,925 B2 * | 6/2005 | Breton et al. | 514/277 |
| 7,030,231 B1 | 4/2006 | Craik et al. | |
| 2003/0198682 A1 | 10/2003 | Gruber et al. | |
| 2004/0126344 A1 | 7/2004 | Mahalingam et al. | |
| 2006/0018851 A1 * | 1/2006 | Patt | 424/62 |
| 2006/0110815 A1 | 5/2006 | Gruber | |
| 2006/0198800 A1 | 9/2006 | Dilallo et al. | |
| 2007/0140999 A1 * | 6/2007 | Puglia et al. | 424/62 |
| 2008/0206169 A1 | 8/2008 | Millikin et al. | |
| 2009/0028826 A1 | 1/2009 | Breton et al. | |

FOREIGN PATENT DOCUMENTS

| | | | | |
|---|---|---|---|---|
| JP | 408188517 A | * | 7/1996 | ............... A61K 7/00 |
| JP | 2003252743 A2 | | 9/2003 | |
| KR | 5095167 A | | 9/2005 | |
| WO | 2008015343 A2 | | 2/2008 | |
| WO | 2008090226 A2 | | 7/2008 | |

OTHER PUBLICATIONS

JP408188517A, English translation abstract. 2 pages.*
Patent Translate WO2008090226 (Golz-Berner et al) translation, Publication date of the patent: Jul. 31, 2008, 8 pages.*
Fujimoto, Hexapeptide derived from baker's yeast and its cosmetic applications. Fragrance Journal, 2008, vol. 36, No. 3, pp. 57-60.*
Ruiz-Maldonado et al.; Postinflammatory Hypopigmentation and Hyperpigmentation; (1997) Semin Cutan Med Surrg. 16(1):36-43.
Tomita et al.; Mechanisms for Hyperpigmentation in Postinflammatory Pigmentation, Urticaria pigmentosa and Sunburn; (1989) Dermatologica 179 Suppl 1:49-53.
Holland et al.; The Role of Inflammation in the Pathogenesis of Acne and Acne Scarring; Semin Cutan Med Surg. Jun. 2005;24(2):79-83).
Pillai, et al.; Ultraviolet radiation and skin aging: roles of reactiveoxygen species, inflammation and protease activation . . . ; (2005) Int J Cosmet Sci. Feb;27(1):17-34.
Bissett, et al.; Photoprotective effect of topical anti-inflammatory agents against ultraviolet radiation-induced chronic skin damage in the hairless mouse; (1990) Photodermatol. Photoimmunol. Photomed. 7:153-8.
Thornfeldt; Chronic inflammation is etiology of extrinsic aging; (2008) Journal of Cosmetic Dermatology,7, 78-82.
Gross J, et al.; Animal Collagenases: Specificity of Action, and Structures of the Substrate Cleavage Site; Biochem Biophys Res Commun 1974;61:605-12.
Smith et al.; Alterations in Human Dermal Connective Tissuewith Age and Chronic Sun Damage; J. Invest. Dermatol., 1962, 39, pp. 347-350.
Fleischmajer et al.; Human Dermal Glycosaminoglycans and Aging; Biochim. Biophys. Acta, 1972, 279, pp. 265-275.
Longas et al.; Evidence for Structural Changes in Dermatan Sulfate and Hyaluronic Acid With Aging; Carbohydr. Res., 1987, 159, pp. 127-136.

(Continued)

*Primary Examiner* — Marcela M Cordero Garcia
(74) *Attorney, Agent, or Firm* — David M. Joyal; Joan M. McGillycoddy

(57) ABSTRACT

Cosmetic compositions comprising a metal-complexed peptide fraction of stressed yeast extracts and/or a calcium influx inhibitor are disclosed, as well as methods of using such compositions to impart exfoliating, anti-aging, anti-lipid, anti-inflammatory, and/or lightening benefits to the skin; and/or lightening benefits to the hair. These compositions are believed to have modulatory activity against at least one biochemical pathway implicated in skin aging, inflammation, lipid synthesis, and melanin production.

24 Claims, No Drawings

(56) References Cited

OTHER PUBLICATIONS

Carrino et al.; Age-related Changes in the Proteoglycans of Human Skin; Archives of Biochemistry and Biophysics vol. 373, No. 1, Jan. 1, pp. 91-101, 2000.

Vogel et al.; Age-dependent changes of biomechanical parameters in skin studies in vitro and in vivo; Z Gerontol. May-Jun. 1994;27(3):182-5.

Lanir et al.; In-Vivo Indentation of Human Skin; J Biomech Eng. Feb. 1990;112(1):63-9).

Kishibe M et al.; Kallikrein 8 is Involved in Skin Desquamation in Cooperation with Other Kallikreins; J. Biol. Chem. 2006; 282: 5834-5841.

Bert et al.; Hyaluronan, hydration and flow conductivity of rat dermis; Biorheology. May-Jun. 1998;35(3):211-9.

Wiest et al.; Native hyaluronic acid in dermatology—results of an expert meeting; J Dtsch Dermatol Ges. Mar. 2008;6(3):176-80.

\* cited by examiner

```
                        SEQUENCE LISTING

<160> NUMBER OF SEQ ID NOS: 1

<210> SEQ ID NO 1
<211> LENGTH: 6
<212> TYPE: PRT
<213> ORGANISM: Saccharomyces cerevisiae

<400> SEQUENCE: 1

Phe Val Ala Pro Phe Pro
1               5
```

COSMETIC USES OF MODIFIED STRESSED YEAST EXTRACTS AND RELATED COMPOSITIONS

RELATED APPLICATIONS

This application claims priority to U.S. Provisional Patent Application Ser. No. 61/238,427, filed Aug. 31, 2009, the contents of which are hereby incorporated by reference in their entirety.

FIELD OF INVENTION

The present invention relates generally to compositions for topical application to the skin or hair which comprise metal-complexed peptide fractions of stressed yeast extracts, as well as the use of such compositions to provide specific benefits to the skin or hair.

BACKGROUND OF THE INVENTION

Consumers continually seek to improve the appearance of their skin and hair. Concerns include visible signs of aging, as well as discoloration or hyper-pigmentation, redness and/or inflammation; and over-production of oils and lipids at the skin surface. Thus there remains a need for products that provide anti-aging, anti-inflammatory, anti-lipid and/or lightening effects.

Skin and hair pigmentation is determined by the level of melanin present in the epidermis or hair fiber. Three different types of melanin are present in the epidermis: DHI-melanin, which is blackish in color; DHICA-melanin, which is brownish; and pheomelanin, which is reddish in color. Melanin is synthesized in specialized organelles called melanosomes within pigment cells (melanocytes), in a process that begins with the action of an enzyme, tyrosinase, on the amino acid tyrosine. Melanin synthesis is regulated by a number of intracellular factors such as the activity of tyrosinase, the activity of micropthalmia-induced transcription factor (MITF), signaling by hormones such as melanocyte-stimulating hormone (MSH), oxidative stress, and other factors.

Inflammation also contributes to skin discoloration and has other deleterious effects on the appearance of skin. Ruiz-Maldonado et al. (1997) *Semin Cutan Med. Surrg.* 16(1):36-43; Tomita et al. (1989) *Dermatologica* 179 Suppl 1:49-53. For example, inflamed acne lesions can lead to scarring (Holland et al. *Semin Cutan Med Surg.* 2005 June; 24(2):79-83); and the cumulative degenerative effects of inflammation have been shown to exacerbate intrinsic (chronological) and extrinsic (photo) aging of human skin. Pillai, et al. (2005) *Int J Cosmet Sci.* February; 27(1):17-34; Bissett, et al. (1990) *Photodermatol. Photoimmunol. Photomed.* 7:153-8; Thornfeldt, C R (2008) *J. Cosmet. Dermatol.* 7:78-82. A key inflammatory mediator, tumor necrosis factor-alpha (TNFa), is believed to be responsible for both acute and chronic skin inflammation.

Collagen synthesis and degradation also play a role in common skin concerns. Reduction in collagen I, the collagen type in skin, is associated with loss of firmness and elasticity of skin and leads to wrinkling associated with aging. Collagen is the body's major structural protein and gives skin strength, durability, and a smooth, plump appearance. It is created by fibroblasts, specialized skin cells located in the dermis, in a process that involves conversion of preprocollagen I to procollagen I and eventually to tropocollagen, the form that forms collagen fibers. Collagen I is degraded in the skin by matrix metalloproteinases (MMPs). Gross J, et al. *Biochem Biophys Res Commun* 1974; 61:605-12. MMPs are a family of related zinc-dependent proteases, including the metalloproteinases (MMP-1, -8, and -13) and gelatinases (MMP-2 and 9).

Hyaluronic acid is another component of skin that plays a role in its aesthetic appearance. Hyaluronic acid is a glycosaminoglycan (GAG) found in the skin, as part of the extracellular matrix (ECM). With age, however, GAG synthesis and overall GAG skin content appear to decline. Smith et al. *J. Invest. Dermatol.,* 1962, 39, pages 347-350; Fleischmajer et al. *Biochim. Biophys. Acta,* 1972, 279, pages 265-275; Longas et al. *Carbohydr. Res.,* 1987, 159, pages 127-136. It is believed that this reduction in GAG contributes to age-related changes in the skin's mechanical properties, including, for example, changes in tissue hydration, as well as plumpness and protection against free radicals. Carrino et al., *Arch Biochem Biophys.* 2000 Jan. 1; 373(1):91-101; Vogel et al., *Z Gerontol.* 1994 May-June; 27(3):182-5; Lanir et al., *J Biomech Eng.* 1990 February; 112(1):63-9); Wiest et al. *J Dtsch Dermatol Ges.* 2008 March; 6(3):176-80; Bert et al. *Biorheology.* 1998 May-June; 35(3):211-9.

The activity of exfoliating enzymes in the skin also plays a role in its aesthetic youthful appearance. In the stratum corneum, skin's outermost layer, cell-to-cell cohesion depends primarily on proteins known as the corneodesmosomes. During skin remodeling and renewal, dead cells are shed from the skin surface by the action of native proteases that break down the corneodesmosomes, thus helping exfoliation. Human tissue Kallikreins (KLKs) are a family of proteases that reside in the stratum corneum and are known to be directly involved in corneodesmosome turnover. Kishibe M et al. *J. Biol. Chem.* 2006; 282: 5834-5841.

Overproduction of lipids also affects the appearance of skin, as well as that of hair. For example, excess secretion of sebum is associated with oily skin, hair, and acne; and excess accumulation of subcutaneous fat can result in cellulite. Cellulite is a lumpy, uneven type of fat, that accumulates primarily on the buttocks and thighs and causes an "orange peel" or "cottage cheese" look. Lipid metabolism is partly controlled by the peroxisome proliferator-activated receptors (PPARs), which form a group of nuclear transcription factors. PPAR-gamma (PPAR-$\gamma$), in particular, is believed to be critical in a feed-forward pathway that favors differentiation of and energy storage by adipocytes.

Many of the physiological processes in play in the development of undesirable skin or hair have counterparts in eukaryotic microorganisms, such as yeast, and yeasts extracts have been used in cosmetic applications. For example, in response to heat, UV radiation, or other stress, yeast are known to produce factors that promote cell proliferation or viability. See, e.g., U.S. Pat. No. 2,239,345. Stressed yeast lysates containing such factors have been described and have been indicated for use in cosmetic applications directed to counteracting the effects of certain stresses on the skin. For example, UV-stressed yeast lysates have been used in cosmetic applications. See, e.g., U.S. Pat. Nos. 5,643,587; 5,676,956; and 5,776,441. More recently, ozone-stressed yeast lysates have been described as useful in protecting skin cells from the harmful effects of ozone. See, e.g., U.S. Pat. Nos. 6,461,857 and 6,858,212 to Scholz et al; and U.S. Pat. Appl. Pub. Nos. 2003/0198682 and 2006/0110815. Nonetheless, these earlier cases failed to recognize certain cosmetic uses and failed to identify active ingredients within the cellular lysates.

Accordingly, there remains a need for better-defined cosmetic compositions that effectively provide additional skin benefits, including exfoliating, anti-aging, anti-lipid, anti-inflammatory, and/or skin (or hair) lightening effects. It is therefore an object of the invention to provide compositions and methods for decreasing melanin synthesis, TNFa production, PPARs signaling, and/or metalloproteinase activity; and/or for increasing collagen synthesis, hyaluronic acid production, and/or KLKs activity. It is a further object of the invention to improve overall appearance of skin and hair, and to lighten the skin and hair as desired, by use of such compositions.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that specific peptide fractions derived from stressed yeast and complexed with metal ions are capable of decreasing melanin synthesis, TNFa production, PPARs signaling and/or collagen degradation, and/or increasing collagen synthesis, hyaluronic acid production, and/or KLKs activity; and thus are beneficial agents for improving the appearance of skin and hair. It has further surprisingly been found that melanin synthesis is decreased by inhibition of calcium influx into pigment cells, providing a novel approach to reducing hyper-pigmentation.

One aspect of the instant invention relates to modified yeast peptide fractions for use in cosmetic compositions. In particular, compositions comprising a modified yeast peptide fraction comprising a peptide comprising SEQ ID NO:1 are provided, where the peptide is complexed with metal ions, preferably divalent metal ions, such as zinc ions. Such compositions find use as anti-lipid, anti-inflammatory and/or skin lightening agents, as well as in enhancing exfoliation and/or treating and/or preventing visible signs of skin aging. In some embodiments, the modified peptide fraction is present in an amount sufficient to decrease at least one of melanin synthesis, TNFa production, and/or PPARs signaling. In some embodiments directed against signs of aging, the modified peptide fraction is present in an amount sufficient to decrease metalloproteinase activity; increase collagen synthesis; increase hyaluronic acid production, and/or increase KLKs activity.

Another aspect of the instant invention relates to cosmetic use of compositions comprising modified yeast peptide fractions comprising metal-complexed peptides comprising SEQ ID NO:1 to provide at least one benefit to human skin. Such benefits include:

(a) treatment and/or prevention of fine lines or wrinkles;
(b) reduction of skin pore size;
(c) improvement in skin thickness, plumpness, and/or tautness;
(d) improvement in skin suppleness and/or softness;
(e) improvement in skin tone, radiance, and/or clarity;
(f) improvement in skin texture and/or promotion of retexturization;
(g) improvement in skin barrier repair and/or function;
(h) improvement in appearance of skin contours;
(i) restoration of skin luster and/or brightness;
(j) replenishment of essential nutrients and/or constituents in the skin;
(k) improvement of skin appearance decreased by menopause;
(l) improvement in skin moisturization and/or hydration;
(m) increase in and/or preventing loss of skin elasticity and/or resiliency;
(n) improvement in procollagen and/or collagen synthesis;
(o) treatment and/or prevention of skin sagging or atrophy;
(p) enhancing exfoliation and/or reducing dryneess;
(q) treatment and/or prevention of skin hyper-pigmentation;
(r) treatment and/or prevention of inflammation, such as redness, swelling, and/or puffiness;
(s) treatment and/or prevention of excess sebum output; and
(t) treatment and/or prevention of cellulite.

The compositions can be applied to skin in need of treatment, such as skin that would benefit from the exfoliating, anti-aging, anti-lipid, anti-inflammatory and/or skin (or hair) lightening effects of the compositions. In some embodiments, an effective amount of the modified yeast peptide fraction is provided in a cosmetically acceptable vehicle and topically applied to an area of skin for a time sufficient to produce the desired effect. Preferred topical formulations include a lotion, cream, ointment, essence, gel, or stick. In certain embodiments, the modified yeast peptide fraction is used to lighten hair.

Still another aspect of the instant invention relates to the use of calcium influx inhibitors to treat hyper-pigmentation. The calcium influx inhibitors can decrease melanin synthesis by blocking calcium entry into pigment-producing cells. Preferred calcium influx inhibitors include modified yeast peptide fractions comprising peptides comprising zinc-complexed SEQ ID NO:1; and the compound 2-aminoethyl diphenylborate. In some embodiments, an effective amount of a calcium influx inhibitor is provided in a cosmetically acceptable vehicle and topically applied to a hyper-pigmented area of skin, to lighten the affected area. In some embodiments, the inhibitor is combined with at least one other skin lightener. In some embodiments, the calcium inhibitor is used to lighten hair.

These and other aspects of the invention will be better understood by reference to the following detailed description of the invention.

DETAILED DESCRIPTION

It has surprisingly been found that a modified yeast peptide fraction comprising a peptide comprising metal-complexed SEQ ID NO:1 is capable of decreasing melanin synthesis by inhibiting calcium influx into pigment cells. It has further surprisingly been found that the modified yeast peptide fraction is capable of decreasing TNFa production, decreasing PPARs signaling, decreasing metalloproteinase activity, increasing collagen synthesis, increasing hyaluronic acid production, and/or increasing KLKs activity.

In view of these findings and others, a topical composition comprising a modified yeast peptide fraction comprising a metal-complexed peptide comprising SEQ ID NO:1 is contemplated to be useful in lightening skin (or hair), reducing inflammation, enhancing exfoliation, and/or controlling lipid over-production, as well as in combating signs of skin damage and skin aging, including reducing fine lines and wrinkles, preserving skin firmness and plumpness, improving skin hydration and resiliency, restoring skin luster and brightness, and counteracting other related signs of skin aging. It is further contemplated that other compounds that inhibit calcium influx into pigment cells can find use in lightening skin and/or hair.

Modified Yeast Peptide Fractions and Metal-Complexed Peptides Thereof

One aspect of the instant invention relates to modified peptide fractions of stressed yeast extracts. The fractions comprise peptides having the sequence shown in SEQ ID NO:1, where there peptides are in complexation with metal ions. "Complexation with metal ions," and related terms such as "metal complex", "metal-complexed", "metal-complexed derivative", "complex with metal ions", and the like, refer herein to a coordination compound of a central peptide connected to surrounding metal ions. The metal ion may be any metal cation capable of forming a complex with one or more negatively-charged amino acid residues of the peptide, including without limitation, ions of alkali metals, alkaline earth metals, transition metals, post-transition metals, lanthanides, actinides, metalloids, and the like, or any combination thereof. Typically, the metal ion will be of the form $M^{+n}$, where M is any metal or metalloid and n is an integer from 1 to 4, typically 1 or 2. In certain preferred embodiments, the metal ion is a divalent metal ion (n=2), such as that of calcium ($Ca^{2+}$), cadmium ($Cd^{2+}$), cobalt ($Co^{2+}$), copper ($Cu^{2+}$), magnesium ($Mg^{2+}$), manganese ($Mn^{2+}$), nickel ($Ni^{2+}$), beryllium ($Be^{2+}$), strontium ($Sr^{2+}$), iron ($Fe^{2+}$), mercury ($Hg^{2+}$), zinc ($Zn^{2+}$), and the like, and combinations thereof. Some particularly preferred embodiments involve zinc ions complexed with a peptide comprising SEQ ID NO:1.

As used herein, "peptide" refers to any composition that includes two or more amino acids joined together by a peptide bond. Peptides may be about 2 to about 200 amino acids or more in length, and generally correspond to a fragment of a full-length protein, where the fragment does not include all the amino acids of the native full-length protein. In some embodiments, the peptide may be from at least about 3, at least about 4, at least about 5, at least about 6, at least about 8, at least about 10, at least about 15, or at least about 20 amino acids in length. In some embodiments, the peptide may be no more than about 200, no more than about 100, no more than about 50, no more than about 30, or no more than about 20 amino acids in length. For example, in some preferred embodiments, the peptide includes less than about 20 amino acids, less than about 15 amino acids, less than about 10 amino acids, or about six amino acids, including the sequence SEQ ID NO:1 (Phe-Val-Ala-Pro-Phe-Pro).

In some embodiments, one or more of the six amino acids in the sequence SEQ ID NO:1 (Phe-Val-Ala-Pro-Phe-Pro) can be conservatively substituted. Suitable conservative substitutions of amino acids are known to those of skill in this art and generally can be made without altering the biological activity of the resulting molecule. Amino acid substitutions are typically of single residues, but may be of multiple residues, either clustered or dispersed along the hexameric sequence. An amino acid can be replaced with a different naturally-occurring or a non-conventional amino acid residue. Such substitutions may be classified as "conservative," where an amino acid residue contained in the peptide is replaced with another amino acid of similar character either in relation to polarity, side chain functionality, and/or size. Examples include substituting Phe with Met, Leu or Tyr; substituting Val with Ile or Leu; or substituting Ala with Gly or Ser.

It further will be appreciated that peptides may contain amino acids other than the 20 amino acids commonly referred to as the 20 naturally-occurring amino acids, and that many amino acids, including the terminal amino acids, may be modified in a given peptide, either by natural processes such as glycosylation and other post-translational modifications, or by chemical modification techniques, such as those well known in the art. Among the known modifications which may be present in peptides of the present invention include, but are not limited to, acetylation, acylation, ADP-ribosylation, amidation, branching, cross-linking, cyclization, disulfide bond formation, demethylation, glycosylation, hydroxylation, iodination, methylation, oxidation, phosphorylation, prenylation, racemization, selenoylation, sulfation, and ubiquitination.

In some embodiments, the peptide consists essentially of an amino acid sequence corresponding to SEQ ID NO: 1. "Consists essentially of" means that the peptide excludes additional sequences and other compositional components that would materially affect the ability of the peptide to effectively decrease melanin synthesis, TNFa production, PPARs signaling, and/or collagen degradation, and/or increase collagen synthesis, hyaluronic acid production, and/or KLKs activity. The ability to affect such functions can be determined by one of ordinary skill in the art using, e.g., assays, such as in vitro assays described herein (see Examples 1-7 and 13 below) or other assays known in the art to test for melanin synthesis, TNFa production, PPARs expression or signaling, collagen synthesis, collagen degradation, hyaluronic acid production, and/or KLKs activity.

The modified yeast peptide fractions of the instant invention can be obtained directly from certain yeasts, e.g., from *Saccharomyces cerevesiae*. For example, the yeast peptide fractions can be obtained from stressed yeast extracts, prepared by growing yeast on nutritional media, e.g., using standard fermentation processes known to those skilled in the art, subjecting the yeast to stress, and then lysing the cells. The growing cells are subjected to one or more stresses, generally at sub-lethal doses. Stresses include, e.g., heat, UV radiation, x-rays, hydrogen peroxide, ozone, pollutants, chemical injury or other adverse conditions. A "stressed yeast" is a yeast that has undergone exposure to one or more such stresses. A "stressed yeast extract" is a lysate obtained from yeast grown on nutritional media that were at some point exposed to one or more stresses and subsequently killed to provide a composition comprising yeast components. "Yeast extract" refers to a lysate obtained from yeast grown on nutritional media and subsequently killed so as to provide a composition comprising yeast components including, but not limited to, cellular protein material, cellular nuclear material, cellular cytoplasmic material, cellular protoplasmic material, cell wall components, and/or the nutrient broth. The term "yeast" can encompass a single yeast cell, multiple yeast cells, and/or a culture of yeast cells.

The yeast used may be of various genus known to those skilled in the art, where it is determined that peptides comprising SEQ ID NO:1 are obtainable therefrom. Without wishing to be bound by theory, it is suggested that yeast respond to stresses, such as UV radiation, by generating cellular components, including proteins, which are capable of counteracting the detrimental effects of the stress, and which surprisingly have been found to also offer different and additional benefits to human skin cells, as taught herein. Expression of such proteins may be induced or up-regulated in response to the stress. The induced or up-regulated proteins include proteins have been termed yeast "heat shock proteins" (hsp), also called "stress response proteins." See, e.g., U.S. Pat. No. 2,239,345. Heat shock proteins are known to improve cell proliferation and/or cell viability in the face of adverse conditions, for example, by replacing cellular functions disabled by the stress, or by acting as molecular chaperones to protect native structures, such as by modifying protein folding.

For example, yeast proteins induced or up-regulated in response to stress, such as UV exposure, can be determined by comparing the proteins present in stressed yeast extracts to those present in extracts of yeast not subjected to the same stress, using for example comparative two-dimensional polyacrylamide gel electrophoresis. See, e.g., U.S. Pat. App. Publ. 2006/0110815. Another approach involves running a yeast gene microarray to identify yeast genes whose expression changes in response to the stress, e.g., to determine which genes are induced, up-regulated, turned off, or down-regulated in response to the stress. Such comparisons can indicate a number of yeast heat shock proteins induced or up-regulated in response to stress, and the identified proteins can be analyzed to determine whether or not they contain SEQ ID NO:1. Different yeasts that may be analyzed include, without limitation: *Arthroascus, Aureobasidium, Botryoascus, Brettanomyces, Candida, Citeromyces, Clavispora, Cryptococcus, Debaryomyces, Dekkera, Filobasidium, Guilliermondella, Hansenula, Haneseniaspora, Hormoascus, Klockera, Kluyveromyces, Leucosporidium, Lipomyces, Malassezia, Metschnikowia, Nadsonia, Nematospora, Oosporidium, Pachysolen, Pachytichospora, Penicillium, Pichia, Prototheca, Rhodosporidium, Rhodotorula, Saccharomyces, Saccharomycodes, Saccharomycopsis, Schizosaccharomyce, Schwanniomyces, Sporobolomyces, Sporopachydermia, Tremella, Trichosporan, Trigonopsis, Torulaspora, Torulopsis, Williopsis, Yarrowia, Zygosaccharomyces* and the like, and any of those found to produce proteins or peptides comprising SEQ ID NO:1 may be used, as well as combinations thereof. SEQ ID NO:1 has also been found in transmembrane proteins of *Saccharomyces cerevisiae* and may also occur in the transmembrane proteins of one or more other species, such as one or more of the other yeast species listed above.

In some embodiments, the yeast used is from the genus *Saccharomyces*. In certain preferred embodiments, the yeast is *Saccharomyces cerevisiae*, also known as Baker's yeast. Also, certain types of yeasts may be excluded in some embodiments. For example, in some embodiments, the yeast used in not a wine yeast (e.g., as described in French Patent No. FR 2904552 and Japanese Patent No. JP 2003252743) and/or not *Candida parapsilosis* (e.g., as described in Korean Patent No. KR 2005095167).

The selected one or more species of yeast can be grown at a controlled temperature on nutritional media, which is also referred to as nutrient media or growth media. Typically the media contains amino acids, peptones, low molecular weight peptide fragments, and other common growth media ingredients. A preferred growth media is "yeast fermentation media," which is described in the Handbook of Microbiological Media, published by CRC Press. Methods for growing yeast are known to those skilled in the art. For example, the yeast can be grown in an open-air fermentation vessel, or by using a sealed biological fermentor, e.g., available from New Brunswick Scientific, Edison, N.J. At some point, the growing cells are subjected to one or more stresses, generally at sub-lethal doses. Stresses include, e.g., heat, UV radiation, x-rays, hydrogen peroxide, ozone, pollutants, chemical injury or other adverse conditions. Typically, the stress is used in an amount to cause a response in the yeast, e.g., to induce production of heat shock proteins, yet that is sub-lethal to the yeast. By sub-lethal it is meant that at least about 1% of the yeast survive after exposure to the stress. In some embodiments, at least about 1%, at least about 10%, at least about 25%, at least about 50%, or at least about 80% of the yeast to survive the treatment.

In some preferred embodiments, the living yeast cells are stressed with UV light, more preferably at 286 nm. As discussed above, the cells respond by producing various protective substances. The cells' biochemical changes can be monitored, for example, by assaying absorption at 256 to 258 nm with a UV spectrophotometer. The degree of UV exposure can affect which proteins, including heat shock proteins, are produced, and the amounts thereof. The yeast may be exposed to the UV for several minutes to several days, depending on yeast type, wavelength used, aeration rates, temperature, and the like. Generally, exposure to UV light is continued for up to several days, until the complex biochemical protective mechanism is complete.

In some embodiments, the yeast are exposed to wavelength(s) of UV radiation for a time period that allows a maximum, near maximum, or appreciable portion of the yeast to produce cellular components effective in providing a benefit to human skin or hair, e.g., in improving the appearance of skin or hair. In certain preferred embodiments, the yeast are exposed to wavelength(s) of UV radiation for a time period that allows a maximum, near maximum, or appreciable portion of the yeast to produce cellular components effective against unwanted skin conditions, including hyper-pigmentation, inflammation, lipid over-production, and/or visible signs of aging. For example, the yeast can be exposed to wavelength(s) of UV radiation for a time period that allows a maximum, near maximum, or appreciable portion of the yeast to produce cellular components capable of decreasing one or more of melanin synthesis, TNFa production, PPARs signaling, and metalloproteinase activity; and/or increasing collagen synthesis, hyaluronic acid production, and/or KLKs activity. In certain preferred embodiments, the yeast are exposed to wavelength(s) of UV radiation for a time period that allows a maximum, near maximum, or appreciable portion of the yeast to produce at least one heat shock protein, more preferably where the heat shock protein(s) include at least one peptide portion capable of decreasing one or more of melanin synthesis, TNFa production, PPARs signaling, and metalloproteinase activity; and/or increasing one or more of collagen synthesis, hyaluronic acid production, and KLKs activity. In certain particularly preferred embodiments, the yeast are exposed to wavelength(s) of UV radiation for a time period that allows a maximum, near maximum, or appreciable portion of the yeast to produce heat shock proteins that include a peptide comprising SEQ ID NO: 1 (Phe-Val-Ala-Pro-Phe-Pro).

The stressed yeast then can be lysed to obtain a stressed yeast extract, for example, fermentation can be brought to a halt by breaking down cell walls with a suitable proteolytic enzyme. The yeast can be lysed by a variety of methods known to one skilled in the art, including but not limited to, enzymes, high-speed agitation, autolysis, changes in growth media, and/or changes in pH. The stressed yeast extract typically contains water-soluble and water-insoluble components. The water-insoluble components may be separated and removed to provide stressed yeast extracts that comprise water-soluble components. For example, the insoluble cell wall material can be separated with centrifuge and cellular protoplasm harvested. In some embodiments, the yeast extract is water-soluble, or substantially water-soluble. "Water-soluble" typically means that 0.1 gram of yeast components dissolve in 1 gram of water.

The stressed yeast extracts may be further purified, as desired, by any number of means known to those skilled in the art including, but not limited to, chromatography, steam distillation, solvent extraction, centrifugation, decantation, filtration, and/or carbon treatment. The stressed yeast extracts can be purified and/or concentrated to give fractions suitable for cosmetic use. For example, the stressed yeast extract may be filtered to remove cellular bodies, odor, and other undesirable materials. A "fraction" as used herein refers to a portion of a yeast extract obtained by at least one purification, separation, and/or concentration procedure. A "peptide fraction" refers to a portion of a yeast extract that has been separated, purified, and/or concentrated to increase yeast peptide components of a yeast extract. As known to those of skill in the art, the fraction can be tested to determine its suitability for cosmetic use. For example, two-dimensional polyacrylamide gel electrophoresis can be performed, and proteins present in a yeast peptide fraction can be identified and/or quantified. The fractions for use in the present invention also may be further concentrated by any means known to those skilled in the art including, but not limited to, evaporation, freeze or spray-drying, lyophylization, steam distillation, and/or belt or drum drying.

In certain preferred embodiments, the extract is fractionated using centrifugation, filtration and/or chromatography systems to isolate a dominant peptide fraction. The stressed yeast extract can be purified to enrich small molecular weight peptides, within a 1000 to 3000 Da range, wherein peptides comprising the hexameric peptide SEQ ID NO:1 (Phe-Val-Ala-Pro-Phe-Pro) is the dominant fraction. The peptides can be substantially isolated from other components of the stressed yeast extract, and preferably include less than the full-length proteins from which they are derived.

In some embodiments, the hexameric peptide itself is synthesized, e.g., using automated chemical synthesis or recombinant means, and re-added to the yeast peptide fraction, e.g., to artificially increase the concentration of the hexameric peptide in the yeast peptide fraction. For example, the relatively short molecules may be synthesized using standard chemical peptide synthesis as a single contiguous peptide. Solid phase synthesis can be used, in which the C-terminal amino acid of the sequence is attached to an insoluble support followed by sequential addition of the remaining amino acids in the sequence. Techniques for solid phase synthesis are described, e.g., by Barany and Merrifield, Solid-Phase Peptide Synthesis; pp. 3 284; in The Peptides: Analysis, Synthesis, Biology. Vol. 2: Special Methods in Peptide Synthesis, Part A.; in Merrifield, et al. (1963) J. Am. Chem. Soc., 85: 2149 2156; and in Stewart et al. (1984) Solid Phase Peptide Synthesis, 2nd ed. Pierce Chem. Co., Rockford, Ill.

The hexameric peptide also can be synthesized using recombinant expression systems. Generally, this involves creating a DNA sequence that encodes the desired peptide, placing the DNA in an expression cassette under the control of a particular promoter, expressing the peptide in a host, isolating the expressed peptide and, if required, renaturing the peptide. See, e.g., U.S. Pat. No. 7,030,231. DNA encoding peptides comprising SEQ ID NO:1 can be prepared by any suitable method including, for example, cloning and restriction of appropriate sequences or direct chemical synthesis by methods such as the phosphotriester method of Narang et al. (1979) Meth. Enzymol. 68: 90 99; the phosphodiester method of Brown et al. (1979) Meth. Enzymol. 68: 109 151; the diethylphosphoramidite method of Beaucage et al. (1981) Tetra. Lett., 22: 1859 1862; and the solid support method of U.S. Pat. No. 4,458,066. Chemical synthesis may produce a single stranded oligonucleotide, which may be converted into double-stranded DNA by hybridization with a complementary sequence or by polymerization with a DNA polymerase using the single strand as a template.

Alternatively, sequences may be cloned and the appropriate subsequences cleaved using appropriate restriction enzymes. The nucleic acid sequence encoding the hexameric peptide can then be ligated into a vector having the appropriate corresponding restriction sites. Appropriate restriction sites can also be added to the nucleic acid encoding the peptide by site-directed mutagenesis. The sequence may be expressed in a variety of host cells, including yeast, E. coli, other bacterial hosts, and various higher eukaryotic cells such as the COS, CHO and HeLa cells lines, as well as myeloma cell lines. The recombinant sequence will be operably linked to appropriate expression control sequences for each host. One of skill would recognize that modifications can be made to peptides without diminishing their biological activity. Some modifications may be made to facilitate the cloning or expression of the molecule. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression vectors can be transferred into the chosen host cell by well-known methods, such as calcium chloride transformation for E. coli and calcium phosphate treatment or electroporation for mammalian cells. Cells transformed by the plasmids can be selected by resistance to antibiotics conferred by genes contained on the expression vectors, such as the amp, gpt, neo and hyg genes. Once expressed, the recombinant peptide(s) can be purified according to standard procedures of the art, including ammonium sulfate precipitation, affinity columns, column chromatography, gel electrophoresis and the like. See, generally, R. Scopes, (1982) Protein Purification, Springer-Verlag, N.Y.; Deutscher (1990) Methods in Enzymology Vol. 182: Guide to Protein Purification, Academic Press, Inc. N.Y. The peptide can be purified and/or concentrated to give a form suitable for cosmetic use. As known to those of skill in the art, the peptide composition can be tested to determine its suitability for cosmetic use, as discussed above. The synthesized peptides comprising SEQ ID NO:1 can then be added to an isolated yeast peptide fraction, as described above. The hexameric peptide as well as yeast peptide fractions comprising the peptide as a dominant fraction are also available commercially, e.g., Peptamide® 6 (INCI name Hexapeptide 11), available from Arch Personal Care Products, L.P., South Plainfield, N.J. (www.archpersonalcare.com).

The yeast peptide fractions can then be modified by complexation with one or more metal ions to give modified yeast peptide fractions. As used herein "modified yeast peptide fraction," along with related terms such as "modified peptide fraction," are used herein to refer to a peptide fraction of a yeast extract that contains one or more metal-complexed peptides, that is at least one peptide complexed with metal ions. For example, the yeast peptide fraction may be washed with an aqueous metal salt solution to form complexes between the metal ions and one or more peptides in the fraction. The metal salt may comprise, without limitation, salts of alkali metals, alkaline earth metals, transition metals, post-transition metals, lanthanides, actinides, metalloids, and the like, or any combination thereof. In certain preferred embodiments, the metal salt is a divalent metal salt, such as that of calcium ($Ca^{2+}$), Copper ($Cu^{2+}$), magnesium ($Mg^{2+}$), manganese ($Mn^{2+}$), beryllium ($Be^{2+}$), zinc ($Zn^{2+}$), and the like; and the salts may include sulfates, bromides, chlorides, phosphates, acetates, and the like. Some particularly preferred embodiments use zinc salts, such as, e.g., zinc bromide, zinc chloride, zinc phosphate, zinc acetate, zinc sulfate, and the like. For example, the yeast peptide fraction may be washed with an aqueous zinc sulfate solution, even more preferably a saturated aqueous zinc sulfate solution, to form zinc complexes with the peptides, including a zinc complex with the peptide comprising SEQ ID NO:1.

After the reaction has proceeded to completion, residual anions and free metal ions, if any, can be removed by ion exchange column chromatography. That is, the metal-complexes formed can be run on an ion exchange column to remove, e.g., excess uncomplexed ions. This can provide metal-complexed peptides that are free, substantially free, or even completely free of metal salts and free metal ions. The resulting composition is a modified peptide fraction of the yeast extract, the modification being the complexation with added metal. The metal-complexed peptide comprising SEQ ID NO:1 may constitute from about 0.001 weight % to about 5 weight %; preferably from about 0.01 weight % to about 3 weight %; and more preferably from about 0.1 weight % to about 2 weight %, or about 0.1 weight %, based on the total weight of this modified peptide fraction of the yeast extract. Other remaining components of the modified yeast peptide fraction may include, e.g., other low molecular weight peptides, oligopeptides, sugar, and oligosachharides. Based on the teachings herein, other approaches will be apparent to those of skill in the art for generating modified yeast peptide fractions comprising metal-complexed peptides comprising SEQ ID NO:1 from suitable yeast peptide fractions.

Cosmetic compositions of the instant invention generally comprise an amount of modified yeast peptide fraction comprising a metal-complexed peptide comprising SEQ ID NO:1 effective to provide a benefit to human skin. In preferred embodiments, the compositions comprise an amount of modified peptide fraction, and/or an amount of metal-complexed peptide comprising SEQ ID NO:1, effective to decrease melanin synthesis, TNFa production, PPARs signaling, and/or metalloproteinase activity; and/or to increase collagen synthesis, hyaluronic acid production, and/or KLKs activity. In certain preferred embodiments, the cosmetic composition comprises an amount of metal-complexed peptide comprising SEQ ID NO:1 from about 0.001 weight % to about 5 weight % based on the total weight of the composition; preferably from about 0.01 weight % to about 3 weight % based on the total weight of the composition; and more preferably from about 0.1 weight % to about 2 weight %, or about 1 weight %, based on the total weight of the composition. The above amounts refer to an "active amount" of the modified yeast peptide fraction, such as the amount of metal-complexed peptide comprising SEQ ID NO:1. The term "active amount" refers to the amount of modified peptide fraction and/or metal-complex peptide comprising SEQ ID NO:1, absent diluent, solvent, carrier, filler or the like. Cosmetic compositions described herein find use as exfoliating, anti-aging, anti-lipid, anti-inflammatory, and/or skin (or hair) lightening agents, e.g., as detailed below.

Cosmetic Use of Modified Yeast Peptide Fractions and Related Compositions

Another aspect of the instant invention relates to cosmetic use of compositions comprising modified yeast peptide fractions comprising a metal-complexed peptide comprising SEQ ID NO:1; and/or other calcium influx inhibitors. The cosmetic compositions surprisingly act to increase one or more of KLKs activity, hyaluronic acid production, and collagen synthesis; and/or to decrease one or more of metallocollagenase activity, PPARs signaling, TNFa production, and melanin synthesis, and accordingly find use in exfoliating, anti-aging, anti-lipid, anti-inflammatory, and/or skin (or hair) lightening products.

In some embodiments, a method for providing at least one benefit to human skin is provided, where the method comprises topically applying to skin in need thereof at least one composition described herein in a cosmetically acceptable vehicle. The composition will comprise an effective amount of a modified yeast peptide fraction; metal-complexed peptide comprising SEQ ID NO:1; and/or other calcium influx inhibitor. An "amount effective" or an "effective amount" to provide a particular benefit to the skin refers to the active amount of modified fraction, metal-complexed peptide, or calcium influx inhibitor sufficient to provide a clinically measurable improvement in the particular manifestation of skin when applied for a sufficient time. Such benefits include without limitation, the following:

(a) treatment and/or prevention of fine lines or wrinkles;
(b) reduction of skin pore size;
(c) improvement in skin thickness, plumpness, and/or tautness;
(d) improvement in skin suppleness and/or softness;
(e) improvement in skin tone, radiance, and/or clarity;
(f) improvement in skin texture and/or promotion of retexturization;
(g) improvement in skin barrier repair and/or function;
(h) improvement in appearance of skin contours;
(i) restoration of skin luster and/or brightness;
(j) replenishment of essential nutrients and/or constituents in the skin;
(k) improvement of skin appearance decreased by menopause;
(l) improvement in skin moisturization and/or hydration;
(m) increase in and/or preventing loss of skin elasticity and/or resiliency;
(n) improvement in procollagen and/or collagen synthesis;
(o) treatment and/or prevention of skin sagging or atrophy;
(p) enhancing exfoliation and/or reducing dryness;
(q) treatment and/or prevention of skin hyper-pigmentation;
(r) treatment and/or prevention of inflammation;
(s) treatment and/or prevention of excess sebum output; and
(t) treatment and/or prevention of cellulite.

The compositions of the invention can be applied to skin in need of treatment, such as skin which suffers from a deficiency or loss in any of the foregoing attributes or conditions, or which would otherwise benefit from the composition's exfoliating, anti-aging, anti-lipid, anti-inflammatory and/or skin lightening effects, e.g., as described herein. For example, the modified peptide fraction comprising a metal-complexed peptide comprising SEQ ID NO:1 and/or other calcium influx inhibitor can be provided in a cosmetically acceptable vehicle, topically applied to a desired area of skin, and allowed to remain on the area in an amount effective to treat and/or prevent an unwanted feature or condition of the skin, and/or to improve the aesthetic appearance of the skin. For example, exfoliating benefits may be realized within minutes, while other benefits may require longer periods of time on the skin.

"Condition of the skin" or "skin condition" is used interchangeably herein with "skin disorder." "Treatment" as used herein, as well as related terms such as "treat" or "treating," refers to eradicating, reducing, ameliorating, or reversing one or more of the unwanted features associated with the skin condition being treated, such that the consumer perceives an improvement or other treatment benefit with respect to the condition. "Prevention" as used herein, as well as related terms such as "prevent" or "preventing," refers to affording skin not yet affected by the condition a benefit that serves to avoid, delay, forestall, or minimize one or more unwanted features associated with the skin condition to be prevented.

Such preventative benefits include, for example, delaying development of the condition, or reducing the duration, severity, or intensity of one or more unwanted features associated with the condition if it eventually develops.

Hyper-Pigmentation

In certain preferred embodiments, the cosmetic compositions described herein can be used to treat and/or prevent hyper-pigmentation of skin and/or that of the hair, for example, to lighten skin or hair. In some particularly preferred embodiments, a composition comprising an effective amount of a modified yeast peptide fraction peptide comprising a metal-complexed peptide comprising SEQ ID NO:1 is topically applied to the skin or hair, for example to an area of hyper-pigmented skin or hair. "Hyper-pigmentation" as used herein and unless otherwise specifically indicated, refers to "melanocyte-mediated hyper-pigmentation," meaning that the coloration is exclusively, mostly, or at least substantially caused by the action of melanocytes, pigment-producing cells that synthesize melanin.

Hyper-pigmentation includes any coloration of an individual's skin or hair that is darker than desired by the individual and that is caused by melanocytes. Such unwanted pigmentation may also be called discoloration. Hyper-pigmented areas of the skin include areas of discrete or mottled hyper-pigmentation. Areas of discrete hyper-pigmentation can be distinct, uniform areas of darker color and may appear as brown spots or freckles on the skin, including marks commonly called pigment spots or "age spots." Areas of mottled hyper-pigmentation of the skin can be dark blotches that are larger and more irregular in size and shape than areas of discrete pigmentation. Areas of hyper-pigmentation also include areas of tanned skin, e.g., skin tanned due to UV exposure. Hyper-pigmented hair includes any shade of hair that is darker than desired.

Skin hyper-pigmentation may be caused by any number of factors, including, for example, genetics, UV or sun exposure, age, scarring, or discoloration due to skin injury, including lacerations, burns, sunburn, acne, or other dermatological conditions, and the like. For example, skin hyper-pigmented areas include melasmic patches. Melasma is a common skin disorder involving facial skin discoloration, particularly prevalent in pregnant women, where it is called chloasma faciei or chloasma. Melasmic (or chloasmic) patches may appear as dark brown, irregular patches on the face, particularly on the upper cheeks, nose, lips, upper lip, and forehead. The patches often develop gradually over time and generally do not itch or otherwise hurt, but may negatively affect an individual's appearance. Skin hyper-pigmentation also refers to areas under the arm, e.g., that have become or are becoming darker than desired.

Skin hyper-pigmentation may or may not include areas under an individual's eyes that are darker than desired by the individual, commonly referred to as "under eye dark circles" or "dark circles." Dark circles are usually round, uniform areas of pigmentation beneath each eye, which may be caused by heredity, allergies, tiredness, or other causes. Treatment of hyper-pigmentation, in some embodiments, excludes treating discoloration and/or bagginess in facial skin below the eyes. Notably, under-eye hyper-pigmentation is not a simple melanocyte-mediated pigmentation problem. See, e.g., U.S. Pat. No. 5,643,587. Etiologies include circulatory malfunctions, such as increased vascular permeability causing leakage beneath the skin surface, inflammation, and exposure to the environment, and the problem generally does not respond well to known hypo-pigmenting or skin whitening compounds. Indeed, the topical composition used to reduce under-eye discoloration in that case included a high percentage of ascorbyl phosphate, which itself is a known skin lightener and thus may have been responsible for the under-eye skin lightening. Example 14 below further confirms that the stressed yeast extracts described in U.S. Pat. No. 5,643,587, do not act to reduce under-eye hyper-pigmentation, in the absence of ascorbyl phosphate and in the absence of metal-complexed peptides of the instant invention.

Treating hyper-pigmentation or hyper-pigmented skin/hair refers to eradicating, reducing, ameliorating, or reversing one or more of the unwanted features associated with hyper-pigmentation, such as producing a perceptible lightening of the skin or hair in the affected area. Lightening hyper-pigmented areas of the skin may be desirable, in particular, in diminishing age spots; lightening a suntan; evening or optimizing skin tones, e.g., in areas of mottled hyper-pigmentation; in treating melasmic and chloasmic patches, freckles, after-burn scars, and post-injury hyper-pigmentation. Preventing hyper-pigmentation or hyper-pigmented skin refers to affording skin, not yet affected by hyper-pigmentation, a benefit that serves to avoid, delay, forestall, or minimize one or more unwanted features associated with skin hyper-pigmentation, such as reducing the darkness or size of hyper-pigmented areas that eventually develop. Modified yeast peptide fractions comprising metal-complexed peptides comprising SEQ ID NO:1 that are capable of treating and/or preventing hyper-pigmented skin can be referred to as "skin lighteners." When used for lightening hair, they can be referred to "hair lighteners." "Lightening" and related terms refer to any process making undesirably dark areas lighter, and includes the concepts of bleaching, hypo-pigmenting, whitening and/or de-pigmenting. Compositions used in hyper-pigmentation applications will comprise an effective amount of modified yeast peptide fraction, and/or metal-complexed peptide(s) comprising SEQ ID NO:1, to treat and/or prevent hyper-pigmentation, such as, e.g., to lighten skin/hair in an affected area.

Pigmentation of the skin (including the lips) and hair is determined by the level and type of melanin present in the epidermis or hair fiber. For example, the greater the epidermal level of DHI-melanin, the darkest type of melanin, the darker the skin. As noted above, melanin is synthesized in specialized organelles called melanosomes within pigment cells (also called pigment-producing cells or melanocytes), and the process begins with the conversion of the amino acid tyrosine to dopaquinone by the enzyme tyrosinase. Most other skin lightening approaches have relied upon tyrosinase inhibitors applied to the skin to decrease melanin synthesis. See, e.g., Korean Patent No. KR 2005095167; and Japanese Patent Nos. JP 2003252743, and JP 61260009. These cases, however, as well as Japanese Patent Nos. JP 2002234828 and JP 2001151631, used extracts obtained from non-stressed yeast, that is, from yeast that had not been exposed to one or more stresses. Without wishing to be bound by theory, it is believed that the modified peptide fractions comprising metal-complexed peptides comprising SEQ ID NO:1 do not rely upon a tryrosine inhibitor to decrease melanin synthesis, but appear to have a different mechanism of action. Indeed, it has been surprisingly found that compositions of the instant invention decrease melanin synthesis by inhibiting calcium influx into pigment cells. Furthermore, it has been surprisingly found that compositions comprising other calcium influx inhibitors also can be used in cosmetic applications against hyper-pigmentation. See Example 1 below.

Accordingly, another aspect of the instant invention relates to cosmetic use of compositions comprising a calcium influx inhibitor for skin and/or hair lightening. A "calcium influx inhibitor" as used herein refers to any compound that acts to decrease, reduce, block, or otherwise inhibit the entry of calcium into pigment cells. The term is used interchangeably herein with "calcium channel inhibitor." Calcium influx inhibitors will include compounds known in the art to regulate calcium entry into pigment cells, such as, without limitation, 2-aminoethyl diphenylborate (2-APB). For example, this compound is known to specifically block calcium entry into cells, including into pigment cells. Other known calcium influx inhibitors include, without limitation, Aminohexahydrofluorene, Bepridil, Calcicludine, Calciseptine, Calmidazolium chloride, Nifedipine, Verapamil, FS2 (Dendroaspis polylepis polylepis), Galanin, Protopine, Tetrahydropalmatine, Somatostatin-14, L-Stepholidinealverine and its salts; as well as manganese and its salts, magnesium and it salts. See, e.g., EP 1419764; Int. Pat. Appl. Pub. No. WO 2006048671; and U.S. Pat. Appl. Pub. No. 2009/0028826. Cosmetic compositions comprising calcium influx inhibitors surprisingly act to decrease melanin synthesis, and accordingly find use in skin or hair lightening products, e.g., for treating and/or preventing skin hyper-pigmentation, or bleaching hair. Calcium influx inhibitors that are capable of treating and/or preventing hyper-pigmented skin also can be referred to as "skin lighteners." When used for lightening hair, they also can be referred to "hair lighteners." Compositions used in hyper-pigmentation applications will comprise an effective amount of one or more calcium influx inhibitors to treat and/or prevent hyper-pigmentation, such as, e.g., to lighten skin/hair in an affected area.

In certain embodiments, compositions of the instant invention comprise a modified peptide fraction comprising a metal-complexed peptide comprising SEQ ID NO:1, and/or other calcium influx inhibitor, in an amount sufficient to decrease melanin synthesis in a given area of skin (or hair) when topically applied thereto. As used herein, "decreasing melanin synthesis" and related expressions refer to reducing the amount of one or more of the different types of melanin biosynthesized in skin and/or deposited in hair, and in particular refers to reducing melanocyte-mediated hyper-pigmentation. Without wishing to be bound by theory, the decrease in melanin is believed to be caused by an inhibition of calcium influx into pigment cells, as noted above. Preferably, the decrease in melanin synthesis results in perceptible lightening of the skin (or hair) receiving treatment, although some melanin biosynthesis persists (and some calcium influx persists). For example, in some embodiments, melanin synthesis is reduced by at least about 10%, at least about 25%, at least about 50%, at least about 75%, or at least about 90%, compared to melanin synthesis in the absence of a composition comprising a skin (or hair) lightener. In some embodiments, calcium influx is reduced by at least about 20%, at least about 40%, at least about 50%, at least about 80%, or at least about 95%, compared to calcium influx in the absence of a composition comprising the skin (or hair) lightener. The extent of melanin synthesis and/or calcium influx can be determined by appropriate assays, e.g., in vitro assays described herein or known in the art. For example, Examples 1 and 13 below provide experimental details of assays for determining calcium influx inhibition and total melanin synthesis.

In some embodiments, the cosmetic compositions for treating and/or preventing hyper-pigmentation, e.g., lightening skin (or hair), further comprise at least one other skin lightener (or at least one other hair lightener). For example, the cosmetic composition comprising a modified peptide comprising a metal-complexed peptide comprising SEQ ID NO:1, and/or other calcium influx inhibitor, in an amount effective to treat and/or prevent hyper-pigmentation may further comprise at least one other skin lightener (or at least one other hair lightener). For example, a tyrosine inhibitor, including any of the tyrosine inhibitors disclosed in KR 2005095167; JP 2003252743 and JP 61260009, may be included, in some embodiments. Any other substances that can be applied to the skin (or hair) to lighten the skin (or hair) may also be used as an additional skin (or hair) lightener with the compositions described herein. Examples of skin lighteners include, without limitation, hydroquinone, kojic acid, licorice and/or its derivatives, ascorbic acid and/or its derivatives, arbutin, bearberry extract, Glycyrrhiza glabra and its derivatives, *Chlorella vulgaris* extract, *perilla* extract, coconut fruit extract, and/or other depigmenting agents. *Perilla* extract is disclosed as a whitening agent, e.g., in U.S. Pat. No. 5,980,904 and Japanese Publications Nos. 07025742, 07187989, 10265322, 2001163759, and 2001181173. Coconut fruit extract is disclosed as a whitening agent in Japanese Patent No. 2896815B2.

Other skin lighteners include extracts of *Butea frondosa, Naringi crenulata, Stenoloma chusana, Azadirachta indica, Glycyrrhiza glabra linn., Morinda citrifolia,* tomato glycolipid, or any combinations thereof, as well as, ascorbyl glucoside, vitamin C, retinol and/or its derivatives, arbutin, *rumex crispus* extract, milk proteins including hydrolyzed milk proteins, N,N,S-tris(carboxymethyl)cysteamine, oleanolic acids, *perilla* oils, placenta extract, saxifragia sarmentosa, juniperic acid, thiodipropionic acid (TDPA), ligusticum chiangxiong hort., asmunda japonica thunb., *stellaria medica* (L.) cyr., sedum sarmentosum bunge, ligusticum lucidum Ait., ilex purpurea hassk, emblica, apigenin, ascorbyl palmitol, carruba polyphenols, hesperitin, inabata polyphenol, isoliquirtigenin, kaempherol-7-neohesperidose, L-mimosine, luteolin, oil-soluble licorice extract P-T(40), oxa acid, phenyl isothiocyanate, cococin, silymarin, T4CA, teterahydro curcumin, unitrienol, ursolic-oleanolic acid, UVA/URSI, or any combinations thereof. Further, it is contemplated that synergistic improvements may be obtained with combinations of one or more such additional skin (or hair) lighteners with compositions of the instant invention, in some embodiments. For example, in some embodiments, the invention relates to synergistic action of one or more compositions described herein with TDPA, e.g., to provide enhanced skin lightening benefits to skin.

Inflammation

In certain preferred embodiments, the cosmetic compositions described herein can be used to treat and/or prevent inflammation, for example, to reduce redness and/or puffiness associated with inflammation of the skin. In some particularly preferred embodiments, a composition comprising an effective amount of a modified yeast peptide fraction comprising a metal-complexed peptide comprising SEQ ID NO:1 is topically applied to the skin, for example to an area of inflamed skin. Inflammation generally is caused by an individual's response to unwanted stimuli, such as, for example, pathogens, toxins, air pollution, physical injury that damages cells, foreign bodies, such as a splinter, burns, chemical irritants, auto-immune reactions, and the like, and may be acute or chronic. Stimuli that produce an inflammatory response in an individual can be referred to as "irritants." Inflammation is generally characterized by five cardinal signs: redness, increased heat, swelling, pain, and loss of function. "Inflamed skin" or an "area of skin affected by inflammation" refers to any skin displaying one or more signs or features associated with inflammation, such as redness, swelling, or puffiness. Inflammatory skin conditions include, without limitation, eczema, edema, occupational dermatitis or contact dermatitis, psoriasis, acne, hives (also known as urticaria), rosacea, or other rashes or allergic reactions in response to irritants, such as poison ivy. Areas of inflammation include areas of the skin affected by such conditions, such as acne lesions, warts, pimples, blotches, and irritated areas, such as areas of redness, swelling, and/or puffiness, as well as areas of scaling, flaking, itching, burning, stinging, tingling, and/or numbing.

Treating inflammation or inflamed skin refers to eradicating, reducing, ameliorating, or reversing one or more of the unwanted features associated with inflammation, such as perceptibly reducing redness, puffiness, and/or swelling of the affected area, or soothing or calming the area. Preventing inflammation refers to affording not yet inflamed skin, a benefit that serves to avoid, delay, forestall, or minimize one or more unwanted features associated with inflammation, such as reducing the extent of swelling that may develop upon exposure to an irritant. Modified yeast peptide fractions comprising metal-complexed peptide comprising SEQ ID NO:1 that are capable of treating and/or preventing inflamed skin can be referred to as "anti-inflammatory agents." Compositions used against inflammation will comprise an effective amount of modified yeast peptide fraction, and/or metal-complexed peptide(s) comprising SEQ ID NO:1, to treat and/or prevent inflammation, such as, e.g., to reduce redness, swelling and/or puffiness of an affected area. In some particular embodiments, methods and compositions of the instant invention are directed to fighting all stages of the acne cycle—before, during, and after a breakout, e.g., preventing acne lesion before they surface, reducing the number of acne lesions that surface, accelerating healing during a breakout, etc.

A key inflammatory mediator involved in inflammation is the cytokine tumor necrosis factor-alpha (TNFa), also known as cachexin, or cachectin. TNFa is believed to be responsible for both acute skin inflammation and chronic inflammation. TNFa is produced mainly by macrophages, as well as other cell types, including lymphoid cells, mast cells, endothelial cells, and fibroblasts, and a local increase in TNFa concentration brings about the cardinal signs of inflammation. Without wishing to be bound by theory, it is believed that modified yeast peptide fractions comprising metal-complexed peptides comprising SEQ ID NO:1 can act to decrease TNFa production, thereby reducing one or more of the unwanted features associated with inflammation, such as redness, puffiness, and/or swelling. See Example 2 below.

In certain embodiments, the compositions of the instant invention comprise modified yeast peptide fraction and/or metal-complexed peptide comprising SEQ ID NO:1 in an amount sufficient to decrease TNFa production in a given area of skin when topically applied thereto. As used herein, "decreasing TNFa production" and related expressions refer to reducing the amount of TNFa produced in response to an irritant, for example, by inhibiting the induction of TNFa in response to the irritant. Preferably, the decrease in TNFa production results in a perceptible reduction in redness, puffiness, and/or swelling of the affected area, although some TNFa production persists. For example, in some embodiments, TNFa production is reduced by at least about 10%, at least about 25%, at least about 50%, at least about 75%, or at least about 90%, compared to TNFa production in the absence of a composition comprising an anti-inflammatory agent. The extent of TNFa production can be determined by appropriate assays, e.g., in vitro assays described herein or known in the art. For example, Example 2 below provides experimental details of assays for determining TNFa production.

In some embodiments, the cosmetic compositions for treating and/or preventing inflammation, e.g., reducing redness or swelling, can further comprise at least one other anti-inflammatory agent, such as anti-acne agents. For example, the cosmetic composition comprising a modified yeast peptide fraction comprising metal-complexed peptide comprising SEQ ID NO:1 in an amount effective to treat and/or prevent inflammation may further comprise at least one other anti-inflammatory agent. Anti-inflammatory agents may include, for example, steroids, hydrocortisone, prednisone, prednisolone, aspirin, aspirin derivatives, aloe vera, willow bark, chamomile, and mixtures thereof; as well as anti-irritants, advanced glycation end-product (AGE) inhibitors, and immune system suppressing agents. In some embodiments, compositions of the invention include anti-acne agents, such as, e.g., salicylic acid. Some such embodiments, further include glycolic acid. However, in some other embodiments, additional anti-acne agents, such as salicylic acid, are excluded. Further, it is contemplated that synergistic improvements may be obtained with combinations of one or more such additional anti-inflammatory agents with compositions of the instant invention in some embodiments.

Lipid Over-Production

In certain preferred embodiments, the cosmetic compositions described herein can be used to treat and/or prevent lipid over-production, for example, to reduce excess sebum output and/or cellulite. In some particularly preferred embodiments, a composition comprising an effective amount of a modified yeast peptide fraction comprising a metal-complexed peptide comprising SEQ ID NO:1 is topically applied to the skin, for example to an area of skin affected by lipid over-production. "Over-production of lipids" or "lipid over-production" refers to any production or secretion of oils and/or production or deposition of subcutaneous fat that is in excess of that desired by the individual. For example lipid over-production includes excess production, secretion, or accumulation of sebum, as well as excess production or accumulation of subcutaneous fat, such as cellulite.

Sebum is an oily secretion containing fat, keratin, and cellular material, produced by sebaceous glands, which are tiny ducts adjacent to hair follicles. Sebum is secreted onto the skin and hair (from the scalp). Excess sebum output is associated with oily skin and hair, and can contribute to conditions such as acne and oily dandruff (seborrheic dermatitis). Such problems are particularly common in adolescents, as the increased levels of sex hormones stimulate sebum over-production. Areas affected by lipid over-production include oily areas of the skin, e.g., oily facial skin or an area of the scalp, as well as areas affected by a skin condition associated with excess sebum output, such as acne lesions.

Cellulite is a lumpy uneven type of subcutaneous fat that accumulates primarily on the buttocks and thighs of many women. A number of factors can cause cellulite including, hereditary, intestinal, circulatory, lymphatic, hormonal, and lifestyle factors. Cellulite is considered unsightly because it gives the tissues underlying the skin an "orange peel" or "cottage cheese" look, and pinching the skin can produce a "mattress appearance" with bulging and pitting of the fatty layer. Areas affected by lipid over-production include areas of cellulite, such as areas of the skin having the "orange peel", "cottage cheese" or "mattress" appearance. The term "treatment of cellulite" includes the amelioration of the visible signs of cellulite.

Treating lipid over-production refers to eradicating, reducing, or ameliorating, or reversing one or more of the unwanted features associated with over-production of lipids. Unwanted features associated with over-production of sebum, e.g., include oily, shiny, acne-prone skin, oily scalp, oily hair, dandruff-prone hair, or undesirable body odors. Unwanted features associated with over-production of subcutaneous fat, e.g., include unsightly areas of cellulite. Treatment benefits include, e.g., reducing the oily appearance of affected skin or hair, controlling surface oil, balancing sebum in oily-prone skin, visibly minimizing pores, reducing undesirable body odor due to accumulation of excess sebum, or improving the appearance of areas affected by cellulite deposition. Preventing lipid over-production refers to affording not yet affected skin a benefit that serves to avoid, delay, forestall, or minimize one or more unwanted features associated with lipid over-production, such as reducing the extent of oiliness, severity of acne, or lumpiness of cellulite, that eventually develops at the treated area. Modified yeast peptide fractions comprising metal-complexed peptides comprising SEQ ID NO:1 that are capable of treating and/or preventing lipid over-production can be referred to as "anti-lipid agents," which can act as, e.g., anti-oil and/or anti-cellulite agents. Compositions used to control lipid over-production will comprise an effective amount of modified yeast peptide fraction and/or metal-complexed peptide(s) comprising SEQ ID NO:1 to treat and/or prevent lipid over-production, e.g., to reduce acne and/or cellulite.

Lipid metabolism is partly controlled by the peroxisome proliferator-activated receptors (PPARs), which form a superfamily of nuclear transcription factors. The PPARs are ligand-dependent intracellular proteins that stimulate transcription of specific genes by binding to specific DNA sequences in the nucleus following activation by the appropriate ligand. PPAR-γ activity, in particular, is governed by binding of small lipophilic ligands, mainly fatty acids, derived from nutrition or metabolic pathways that themselves are often controlled by PPAR-γ. Indeed, it is believed that PPAR-γ a is the centerpiece of a feed-forward pathway that favors differentiation of and energy storage by adipocytes. Without wishing to be bound by theory, it is believed that the modified yeast peptide fractions comprising metal-complexed peptides comprising SEQ ID NO:1 can act to decrease PPARs signaling, particularly that of PPAR-γ, thereby reducing lipid production and acting as anti-oil and/or anti-cellulite agents. For example, the compositions may act to decrease induction of PPAR-γ, so that less is available for signaling adipocyte differentiation and fat storage. See Example 3 below.

Further, it can be noted that the lipids whose production is reduced by certain compositions of the instant invention are distinguished from membrane lipids, such as those found in lipid bilayers. Bilayer lipids include, for example, lipids in the bilayers of the stratum corneum, or other cutaneous lipids, such as cholesterol, cholesterol esters, free fatty acids, and ceraminades that make up the lipid bilayers of skin. See, e.g., U.S. Pat. Appl. Pub. No. 2006/0110815.

In certain embodiments, the compositions of the instant invention comprise a modified yeast peptide fraction and/or metal-complexed peptide comprising SEQ ID NO:1 in an amount sufficient to decrease PPARs signaling in a given area of skin when topically applied thereto. As used herein, "decreasing PPARs signaling" and related expressions refer to reducing the extent to which one or more PPARs (in particular PPAR-γ) can signal a cell to produce and/or store lipids, e.g., by decreasing the expression of PPAR-γ. Preferably, the decrease in PPARs signaling results in a perceptible reduction in oil or cellulite at an affected area, although some PPARs signaling and lipid production persists. For example, in some embodiments, PPARs expression and/or signaling is reduced by at least about 10%, at least about 25%, at least about 50%, at least about 75%, or at least about 90%, compared to PPARs expression and/or signaling in the absence of a composition comprising an anti-lipid agent. The extent of PPARs expression and/or signaling can be determined by appropriate assays, e.g., in vitro assays described herein or known in the art. For example, Example 3 below provides experimental details of assays for determining PPAR-γ expression.

In some embodiments, the cosmetic compositions for treating and/or preventing lipid over-production, e.g., reducing sebum output or cellulite, can further comprise at least one other anti-lipid agent. For example, the cosmetic composition comprising a modified yeast peptide fraction comprising a metal-complexed peptide comprising SEQ ID NO:1 in an amount effective to treat and/or prevent lipid over-production may further comprise at least one other anti-lipid agent. Examples include, without limitation, certain anti-acne agents and other PPAR inhibitors, e.g., extracts from *Alisma orientate*. See, e.g., U.S. Pat. No. 7,410,658. Further, it is contemplated that synergistic improvements may be obtained with combinations of one or more such additional anti-lipid agents with compositions of the instant invention, in some embodiments.

Signs of Aging

In certain preferred embodiments, the cosmetic compositions described herein can be used to treat and/or prevent signs of skin aging or other skin damage. Signs of skin aging include any dermatological signs of aging, including signs caused by intrinsic (chronological) aging, or caused by extrinsic factors (such as in photoaging). The compositions may be applied to skin already showing visible signs of aging, or likely to show such signs, e.g., due to age or sun exposure.

An early sign of skin aging involves the gradual development of facial wrinkles, whether fine surface lines or deeper creases and folds. While wrinkling and other signs of aging are intrinsic to skin, the process may be accelerated by external factors, such as excessive exposure to the sun and other damaging elements, overactive facial expression muscles, frequent use of tobacco products, poor nutrition, or certain skin disorders. Fine surface lines that progress to deeper creases, deepening facial wrinkles due to repeated skin folding, and deep folds that develop with maturity are visible changes associated with aging.

Treating signs of skin aging refers to eradicating, reducing, ameliorating, or reversing one or more of the unwanted features associated with skin aging, e.g., by reducing loss of skin firmness or plumpness to a perceptible extent. For example, compositions and methods of the instant invention may be used to reverse or treat signs of skin aging once manifested, such as is common in individuals over 25 years of age. Preventing signs of skin aging refers to affording skin a benefit that serves to avoid, delay, forestall, or minimize one or more unwanted features associated with aging, e.g., by slowing the loss of firmness or plumpness as the skin eventually ages. That is, the compositions and methods of the instant invention may be employed prophylactically, e.g., to forestall signs of skin aging in individuals that have not yet manifested signs of skin aging, most commonly in individuals under 25 years of age.

Modified yeast peptide fractions comprising metal-complexed peptides comprising SEQ ID NO:1 that are capable of treating and/or preventing signs of aging can be referred to as "anti-aging agents." Compositions used to as anti-aging agents will comprise an effective amount of a modified yeast peptide fraction and/or metal-complexed peptide comprising SEQ ID NO:1 to treat and/or prevent signs of aging. Some particularly preferred embodiments provide compositions for topical application which comprise an effective amount of a zinc-complexed peptide comprising SEQ ID NO:1 to treat and/or prevent signs of aging. Treatment and/or prevention generally results in an improvement in one or more unwanted features and/or in the overall aesthetic appearance of the treated skin.

The improvement in the unwanted feature and/or overall aesthetic appearance can include one or more of the following: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing skin atrophy; improving skin tone, radiance, and/or clarity; preventing, reducing, and/or ameliorating skin sagging; improving skin firmness, plumpness, tautness, suppleness and/or softness; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause, such as essential nutrients or other skin constituents; ameliorating the effects of estrogen imbalance; improving communication among skin cells; increasing cell proliferation and/or multiplication; increasing skin cell metabolism decreased by aging and/or menopause; retarding cellular aging; improving skin moisturization and/or hydration; enhancing skin thickness; increasing skin elasticity and/or resiliency; improving procollagen and/or collagen synthesis; enhancing exfoliation; improving microcirculation; reducing dryness; and any combinations thereof.

In certain preferred embodiments, the compositions and methods of the invention are directed to the treatment and/or prevention of fine lines or wrinkles in the skin. In the case of treatment, the compositions are applied to skin in need of such treatment, by which is meant skin having wrinkles and/or fine lines. The fine lines and/or wrinkles may occur on any surface of the skin, including without limitation, the skin of the hands, arms, legs, neck, chest, and face, including the forehead. Preferably, the compositions are applied directly to the fine lines and/or wrinkles. For example, methods for treating fine lines and wrinkles may comprise topically applying a composition described herein to skin in need thereof, e.g., topically applying directly to a fine line and/or wrinkle in an amount and for a time sufficient to reduce the severity of the fine lines and/or wrinkles. The effect of a composition on the appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin).

The term "wrinkle" or "wrinkling" refers to both fine wrinkling and/or coarse wrinkling. Fine wrinkling or fine lines refers to superficial lines and wrinkles on the skin surface. Coarse wrinkling refers to deep furrows, particularly deep lines/wrinkles on the face and around the eyes, including expression lines such as frown lines and wrinkles, forehead lines and wrinkles, crow's feet lines and wrinkles, nasolabial folds, and marionette lines and wrinkles. Forehead lines and wrinkles refer to superficial lines and/or deep furrows on skin of the forehead. Crow's feet lines and wrinkles refer to superficial lines and/or deep furrows on skin around the eye area. Marionette lines and wrinkles refer to superficial lines and/or deep furrows on skin around the mouth.

In certain preferred embodiments, the compositions and methods of the instant invention are directed to improving skin firmness, plumpness, and/or tautness. In certain preferred embodiments, the compositions and methods of the instant invention are directed to increasing and/or preventing loss of skin elasticity. Elasticity of skin refers to the skin's springiness and/or resilience, due to the skin's ability to regain its original shape and size after deformation. Elasticity of the skin may be evaluated by a pinch test that can cause deformation by either stretching or squeezing the skin.

Loss of firmness, wrinkling and other signs of aging result in part from loss of skin collagen over time. As used herein "collagen" is used interchangeably with "collagen I" or "collagen type I," the type present in skin as a dermal matrix component. Collagen I is composed of three protein chains wound together in a tight triple helix, which provides a tensile strength greater than that of steel. It is created by fibroblasts, specialized skin cells located in the dermis. Formation involves the production of preprocollagen I by ribosomes along the rough endoplasmic reticulum (RER); conversion to procollagen I and formation of the triple helical structure within the RER; and eventual formation of tropocollagen outside the cell, the form that aggregates to give collagen fibrils and then fibers. Collagen gives skin firmness, strength, durability, and a youthful smooth, plump appearance. Without wishing to be bound by theory, it is believed that the modified yeast peptide fractions comprising metal-complexed peptides comprising SEQ ID NO:1 can act to increase collagen production and thus collagen skin levels, thereby delaying one or more of the unwanted features associated with skin aging, e.g., by instead maintaining skin firmness and plumpness. See Example 4 below.

In certain embodiments, the compositions of the instant invention comprise a modified yeast peptide fraction and/or metal-complexed peptide comprising SEQ ID NO:1 in an amount sufficient to increase collagen synthesis in given area of skin when topically applied thereto. As used herein, "increasing collagen synthesis" and related expressions refer to stimulating, inducing, or up-regulating procollagen and/or collagen production to increase the collagen content in an area of skin, preferably improving skin firmness and/or plumpness to a perceptible extent. For example, in some embodiments, collagen synthesis is increased by at least about 10%, at least about 25%, at least about 50%, at least about 75%, or at least about 90%, compared to the synthesis of collagen in the absence of the composition. The extent of collagen and/or collagen synthesis in the skin can be determined by appropriate assays, e.g., in vitro assays described herein or known in the art. The levels of one or more collagen precursors can also be determined as indicative of the level of skin collagen, and such in vitro assays are also known in the art. For example, Example 4 below provides experimental details of assays for measuring procollagen I levels in human dermal fibroblasts.

While collagen is created by fibroblasts, its degradation is normally controlled by the matrix metalloproteinases (MMPs). Gross J, et al. *Biochem Biophys Res Commun* 1974; 61:605-12. MMPs are a family of related zinc-dependent proteases having over 25 members and including the metalloproteinases (MMP-1, -8, and -13) and the gelatinases (MMP-2 and 9). Degradation of collagen by MMPs is associated with loss of firmness and elasticity of the skin. For example, collagen degradation leads to abnormal cross-linking of the collagen fibers to produce rigid, less flexible structures. Without wishing to be bound by theory, it is believed that the modified yeast peptide fractions comprising a metal-complexed peptide comprising SEQ ID NO:1 can act as metalloproteinase inhibitors, decreasing metalloproteinase activity and thereby reducing loss of collagen and associated unwanted features of skin aging. See Example 5 below.

In certain embodiments, the compositions of the instant invention comprise a modified yeast peptide fractions comprising a metal-complexed peptide comprising SEQ ID NO:1 in an amount sufficient to decrease metalloproteinase activity in given area of skin when topically applied thereto. As used herein, "decreasing metalloproteinase activity" and related expressions refer to inhibiting, down-regulating, or reducing the activity of one or more enzymes of the metalloproteinase superfamily. Preferably, the decrease in metalloproteinase activity reduces collagen loss in the skin to a perceptible extent, although some metalloproteinase activity persists. For example, in some embodiments, metalloproteinase activity is reduced by at least about 10%, at least about 25%, at least about 50%, at least about 75%, or at least about 90%, compared to the activity of the metalloproteinase in the absence of a composition comprising a metalloproteinase inhibitor. The extent of metalloproteinase activity and/or inhibition can be determined by appropriate assays, e.g., in vitro assays described herein or known in the art. For example, Example 5 below provides experimental details of assays for measuring metalloproteinase activity and inhibition.

Loss of hyaluronic acid over time also plays a role in skin aging. Hyaluronic acid is a glycosaminoglycan (GAG) found in the skin as part of the ECM. GAGs are long unbranched polymers of repeating disaccharide units, mainly composed of hexosamine, hexose, hexuronic acid moieties, or sulfates thereof. GAGs bind to proteins in the skin to form proteoglycans, which contribute to the growth, preservation, and repair of skin. Hyaluronic acid, in particular, has been reported to be responsible for hydration of the skin, nutrient exchange, and protection against free radicals. Wiest et al. *J Dtsch Dermatol Ges.* 2008 March; 6(3):176-80; Bert et al. *Biorheology.* 1998 May-June; 35(3):211-9. It also has been reported, however, that as skin ages over time, GAG synthesis declines and the overall GAG content in the skin decreases. Smith et al. in *J. Invest. Dermatol.*, 1962, 39, pages 347-350; Fleischmajer et al. *Biochim. Biophys. Acta,* 1972, 279, pages 265-275; Longas et al. *Carbohydr. Res.*, 1987, 159, pages 127-136. This reduction in GAG and hyaluronic acid content in the skin is believed to contribute to age-related changes in the mechanical properties of skin, particularly changes in tissue hydration and resiliency. Carrino et al., *Arch Biochem Biophys.* 2000 Jan. 1; 373(1):91-101; Vogel et al., *Z Gerontol.* 1994 May-June; 27(3):182-5; Lanir et al., *J Biomech Eng.* 1990 February; 112(1):63-9). Without wishing to be bound by theory, it is believed that the modified yeast peptide fractions comprising a metal-complexed peptide comprising SEQ ID NO:1 can act to increase hyaluronic acid production, thereby reducing one or more of the unwanted features associated with skin aging, e.g., by improving skin hydration and resiliency. See Example 6 below.

In certain preferred embodiments, the compositions and methods of the instant invention are directed to improving skin moisturization and/or hydration. For example, in certain embodiments, the compositions of the instant invention comprise a modified yeast peptide fraction comprising a metal-complexed peptide comprising SEQ ID NO:1 in an amount sufficient to increase hyaluronic acid production in a given area of skin when topically applied thereto. As used herein, "increasing hyaluronic acid production" and related expressions refer to stimulating, inducing, or up-regulating hyaluronic acid synthesis to increase the hyaluronic acid content in an area of skin, preferably improving skin hydration and/or resiliency by a perceptible amount. For example, in some embodiments, hyaluronic acid production is increased by at least about 10%, at least about 25%, at least about 50%, at least about 75%, or at least about 90%, compared to the production of hyaluronic acid in the absence of the composition. The extent of hyaluronic acid and/or hyaluronic acid production in the skin can be determined by appropriate assays, e.g., in vitro assays described herein or known in the art. For example, Example 6 below provides experimental details of assays for measuring hyaluronic acid levels in human dermal fibroblasts.

Exfoliating enzymes in the skin, such as the KLKs, are also involved in skin aging. KLKs are a family of proteases residing in the stratum corneum of human skin that aid exfoliation of dead skin cells by breaking down proteins responsible for cell-to-cell cohesion. Kishibe M et al. 2006 "Kallikrein 8 Is Involved in Skin Desquamation in Cooperation with Other Kallikreins." J. Biol. Chem. 282: 5834-5841. In the stratum corneum, cell-to-cell cohesion depends primarily on proteins known as the corneodesmosomes. Corneodesmosomes are known to be broken down by KLKs during skin remodeling and renewal, allowing dead cells to slough off of the skin surface. This exfoliation of dead cells improves the skin's aesthetic appearance, e.g., by preventing build up of dead cells on the skin surface that give the skin a dry, rough, dull appearance. Exfoliation can leave skin feeling smoother and looking fresher, and may also augment penetration of other skin actives. It is believed that with age, however, corneodesmosome turnover slows down, allowing a build up of dead cells on the skin surface. Without wishing to be bound by theory, it is believed that the modified yeast peptide fractions comprising metal-complexed peptide comprising SEQ ID NO:1 can act to increase KLKs activity, thereby reducing one or more unwanted features associated with skin aging, e.g., reducing dryness and/or improving skin luster and/or brightness. See Example 7 below. Up-regulation of KLK activity can increase the rate of shedding dead skin, and thus naturally enhance skin exfoliation.

Accordingly, in certain preferred embodiments, the compositions described herein can be used to enhance exfoliation. In some particularly preferred embodiments, a composition comprising an effective amount of a modified yeast peptide fraction and/or metal-complexed peptide comprising SEQ ID NO:1 is topically applied to the skin, e.g., to an area of skin in need of exfoliation. An area of skin in need of exfoliation includes any skin surface that would benefit from an increase in the rate of removal of dead cells building up on the skin surface, for example, as may be common in individuals over 25 years of age, and in particular areas of dry skin. Exfoliation of dry skin can produce a fresher, smoother look of the area. Areas of skin in need of exfoliation also include areas where it is desirable to increase or augment penetration of a skin active being topically delivered. Areas of skin in need of exfoliation also include areas prone to acne, e.g., where exfoliation can help stop acne before it starts, e.g., by removing pore-clogging dirt and oil to reveal fresher, brighter skin and/or a shine-free finish. Areas that can benefit from enhanced exfoliation include, without limitation, the skin of the hands, arms, legs, neck, chest, and face, including the forehead. In particular, the skin of the joints and feet tend to accumulate dead skin cells, leading to rough, dry, dull, wrinkled, and/or discolored skin in such areas.

In some even more preferred embodiments, a composition described herein is topically applied to the skin of the elbows, knees, ankles, feet, soles of the feet, heels, and the like, areas that may particularly benefit from enhanced exfoliation. In some preferred embodiments, a composition described herein is topically applied an area of dry skin, areas that typically also benefit from enhanced exfoliation. Modified yeast peptide fractions comprising metal-complexed peptides comprising SEQ ID NO:1 that are capable of enhancing exfoliation can be referred to as "exfoliating agents." Compositions used to as exfoliating agents will comprise an effective amount of modified yeast peptide fraction and/or metal-complexed peptide(s) comprising SEQ ID NO:1 to improve or enhance exfoliation in a given area of skin when topically applied thereto.

More particularly, in certain embodiments, compositions of the instant invention comprise a modified yeast peptide fraction comprising metal-complexed peptide comprising SEQ ID NO:1 in an amount sufficient to increase KLKs activity in a given area of skin when topically applied thereto. As used herein "increasing KLKs activity" and related expressions refer to stimulating, inducing, or up-regulating the proteolytic activity of one or more protease enzymes of the KLKs family, to increase removal of dead skin cells from an area of skin. Preferably, the increase in KLKs activity increases the rate of exfoliation of dead cells from the skin surface to a perceptible extent, such that, for example, an improvement is observed in skin luster and/or brightness; and/or an improvement is observed in skin tone, radiance, and/or clarity. For example, in some embodiments, KLKs activity is increased by at least about 10%, at least about 25%, at least about 50%, at least about 75%, or at least about 90%, compared to the activity of the KLK protease in the absence of the composition. The extent of exfoliation and/or KLKs activity in the skin can be determined by appropriate assays, e.g., in vitro assays described herein or known in the art. For example, Example 7 below provides experimental details of assays for measuring the activity of recombinant human KLK5.

In some embodiments, methods for enhancing exfoliation further comprise rubbing the composition comprising an exfoliating agent against the skin surface. Such rubbing generally involves pressing the composition against the skin, and moving it around on the skin, preferably repeatedly, and more preferably repeatedly in circular motions. By "repeatedly" is meant about two, about three, about five, about ten times or more, e.g., to help slough away dead skin cells loosened by the proteolytic-enhancing properties of the composition. Rubbing may be gentle or vigorous, depending, e.g., on the area being exfoliated. Following exfoliation, the area of skin generally is rinsed, for example, with cool water, and then moisturized to protect the exfoliated skin surface.

In certain embodiments, the compositions of the instant invention comprise a modified yeast peptide fraction comprising a metal-complexed peptide comprising SEQ ID NO:1 in an amount sufficient to bring about two or more of the following: increase in KLKs activity, increase in hyaluronic acid production, increase in collagen synthesis, and decrease in metalloproteinase activity, in a given area of skin when topically applied thereto. Without wishing to be bound to theory, two or more such combined actions, targeted against different aging processes, may have synergistic results in treating and/or preventing signs of skin aging.

Further, the skin-lightening, anti-inflammatory, and/or anti-lipid properties of the compositions described herein can also contribute to their anti-aging properties. For example, inflammation has been shown to activate various matrix degrading metalloproteases, leading to abnormal matrix degradation that may contribute to skin aging. Pillai, et al. (2005) *Int J Cosmet Sci*. February; 27(1):17-34. Inflammation also has been shown to exacerbate intrinsic and extrinsic aging of human skin by causing an accumulation of reactive oxygen species, which damage cellular proteins, lipids and carbohydrates that then accumulate in dermal and epidermal compartments. Pillai, et al. (2005) *Int J Cosmet Sci*. February; 27(1): 17-34; Bissett, et al. (1990) *Photodermatol. Photoimmunol. Photomed.* 7:153-8; Thornfeldt, C R (2008) *J. Cosmet. Dermatol.* 7:78-82. Inflammation is known to also contribute to skin discoloration, for example, hyper-pigmentation in the skin has been observed post-inflammation. Ruiz-Maldonado et al. (1997) *Semin Cutan Med Surg.* 16(1):36-43; Tomita et al. (1989) *Dermatologica.* 179 Suppl 1:49-53); Holland et al. *Semin Cutan Med Surg.* 2005 June; 24(2):79-83. Skin discoloration, along with oiliness and/or areas of cellulite, can further contribute to an appearance of aging. Again without wishing to be bound to theory, the combined actions of compositions described herein can provide synergistic skin benefits, in certain embodiments, e.g., by exhibiting two or more of the following modulatory activities: decreasing melanin synthesis, decreasing TNFa production, decreasing PPARs signaling, decreasing metalloproteinase activity, increasing collagen synthesis, increasing hyaluronic acid production, and increasing KLKs activity.

In some embodiments, the cosmetic compositions for treating and/or preventing signs of skin aging can further comprise additional exfoliating and/or anti-aging agents. For example, the cosmetic composition comprising a modified yeast peptide fraction comprising metal-complexed peptide comprising SEQ ID NO:1 in an amount effective to treat and/or prevent signs of skin aging may further comprise at least one other exfoliating and/or anti-aging agent. It is contemplated that synergistic improvements may be obtained with such combinations, in some embodiments.

Exemplary exfoliating agents include, without limitation, alpha-hydroxyacids, beta-hydroxyacids, oxaacids, oxadiacids, and their derivatives such as esters, anhydrides, and salts thereof. Suitable hydroxy acids include, for example, glycolic acid, lactic acid, malic acid, tartaric acid, citric acid, 2-hydroxyalkanoic acid, mandelic acid, salicylic acid, and derivatives thereof, as well as fruit enzymes, such as pineapple enzyme. A preferred additional exfoliating agent is glycolic acid Exemplary anti-aging agents include, without limitation, botanicals (e.g., *Butea Frondosa* extract); thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; antioxidants, exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; anti-aging botanicals, keratolytic agents, desquamating agents, keratinocyte proliferation enhancers, and skin plumpers that serve as additional collagen enhancers to the skin, to name a few. An example of a suitable skin plumper is palmitoyl oligopeptide. Other skin plumpers include other collagen and/or other glycosaminoglycan (GAG) enhancing agents. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof. In some embodiments, the invention relates to synergistic action of one or more compositions described herein with TDPA, e.g., to provide enhanced anti-aging benefits to skin. Additional examples of anti-aging agents are provided below.

Based on the teachings provided herein, one of skill in the art will recognize other cosmetic and/or pharmaceutical applications for the compositions described herein, and such applications are also contemplated as within the scope of the instant invention. For example, compositions described herein may also find use in personal care products, such as skin care products or hair care products, where it is desirable to produce a skin benefit described herein upon application of the product. Personal care products for the skin include, for example, underarm deodorants. It is contemplated, for example, that compositions described herein can find use in underarm formulations that lighten the skin under the arms, e.g., where the under-arm area has become or is becoming darker than desired.

The invention provides methods for providing a skin benefit by topically applying a composition comprising a modified yeast peptide fraction comprising metal-complexed peptide comprising SEQ ID NO:1, and/or other calcium influx inhibitor, over an area of skin for a period of time sufficient to produce one or more of the benefits described herein. The composition will typically be applied to the skin one, two, or three times daily for as long as is necessary to achieve desired results, such as the exfoliating, anti-aging, anti-lipid, anti-inflammatory and/or skin (or hair) lightening benefits, as described herein. This treatment regiment may comprise daily application or every-other-day application for at least about one week, at least about two weeks, at least about four weeks, at least about eight weeks, at least about twelve weeks, or more. For example, in some embodiments directed against acne, inventive compositions may be applied morning and/or evening, e.g., by gently smoothing the product over the face, preferably to cleansed dry skin. Chronic treatment regimens are also contemplated, e.g., with respect to prophylactic treatments aimed at forestalling one or more signs of skin aging or other unwanted skin features, such as acne.

The cosmetic compositions described herein find use in exfoliating, anti-aging, anti-lipid, anti-cellulite, anti-inflammatory, and/or skin (or hair) lighting products, preferably formulated for topical application to the skin (or hair), e.g., with a cosmetically acceptable vehicle, as detailed below.

Cosmetic Formulations of Modified Peptide Fractions & Related Compositions

The compositions described herein can be formulated as a variety of skin or hair care products for topical application. The composition may be formulated in a variety of product forms suitable for application to the skin (including the scalp) and/or hair, such as, for example, a lotion, cream, serum, spray, aerosol, cake, ointment, essence, gel, paste, patch, pad, pencil, pomade, solution, towelette, mask, stick, foam, elixir, mousse, powder, bath salt, foaming cleanser, concentrate, or any other liquid, semi-solid, or solid form. Topical application to the hair includes, e.g., topical application to a hair follicle. Preferably the composition is formulated as a lotion, cream, essence, ointment, or gel, and in particular a lotion, toner pad or cleanser, e.g., for anti-acne products. Exemplary formulations for an essence are provided in Examples 8, 9, and 13, below. Exemplary formulations for a cream formula and a daytime cram formula are provided below in Examples 10 and 11, respectively. Exemplary formulation for a foaming cleanser formulation is provided in Example 12 below.

The compositions will comprise an effective amount of a modified yeast peptide fraction, and/or metal-complexed peptide comprising SEQ ID NO:1, and/or calcium influx inhibitor, by which is meant an amount sufficient to impart to the formulated product one or more desired properties or modulatory activities, such as acting as a skin (or hair) lightener, anti-inflammatory agent, anti-lipid agent, exfoliating agent, and/or an anti-aging agent. For example, the modified peptide fraction or metal-complexed peptide comprising SEQ ID NO:1 may be present in an amount from about 0.001 weight % to about 5 weight % based on the total weight of the composition; preferably from about 0.01 weight % to about 3 weight % based on the total weight of the composition; and more preferably from about 0.1 weight % to about 2 weight %, or about 1 weight %, based on the total weight of the composition.

The compositions can include a cosmetically acceptable vehicle. A cosmetically acceptable vehicle refers to any vehicle, for a cosmetic, drug or medicament that is suitable for use in direct, safe contact with human tissues and/or human hair, and may include, e.g., any diluent, solvent, carrier, filler, or the like. Such vehicles may take the form of any known in the art suitable for application to skin (or hair) and may include water (e.g., deionized water); vegetable oils; mineral oils; esters such as octal palmitate, isopropyl myristate, and isopropyl palmitate; ethers such as dicapryl ether and dimethyl isosorbide; alcohols such as ethanol and isopropanol; fatty alcohols such as cetyl alcohol, cetearyl alcohol, stearyl alcohol, and biphenyl alcohol; isoparaffins such as isooctane, isododecane, and isohexadecane; silicone oils such as cyclomethicone, dimethicone, dimethicone cross-polymer, polysiloxanes, and their derivatives, preferably organo-modified derivatives; hydrocarbon oils such as mineral oil, petrolatum, isoeicosane, and polyisobutene; polyols such as propylene glycol, glycerin, butylene glycol, pentylene glycol, and hexylene glycol; waxes such as beeswax and botanical waxes; or any combinations or mixtures of the foregoing. Based on the teachings herein, a person skilled in the art will be able to select a suitable vehicle, and/or in an amount thereof, such that one or more of the desired properties of the cosmetic compositions of the instant invention can be preserved.

The vehicle may comprise an aqueous phase, an oil phase, an alcohol phase, a silicone phase, or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions, or the like having the appearance of a cream, gel, or microemulsions. The emulsion may include an emulsifier, such as a nonionic, anionic or amphoteric surfactant.

The oil phase of the emulsion preferably has one or more organic compounds, including emollients; humectants, such as butylene glycol, propylene glycol, Methyl gluceth-20, and glycerin; other water-dispersible or water-soluble components, including thickeners such as veegum or hydroxyalkyl cellulose; gelling agents, such as high MW polyacrylic acid, such as CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate, and isopropyl palmitate; ethers such as dicapryl ether; fatty alcohols such as cetyl alcohol, stearyl alcohol, and behenyl alcohol; isoparaffins such as isooctane, isododecane, and isohexadecane; silicone oils such as dimethicones, cyclic silicones, and polysiloxanes; hydrocarbon oils such as mineral oil, petrolatum, isoeicosane, and polyisobutene; natural or synthetic waxes; and the like. The oil-containing phase may be composed of a single oil or mixtures of different oils. Suitable hydrophobic hydrocarbon oils may be saturated or unsaturated, have an aliphatic character, be straight or branched chained, or contain alicyclic or aromatic rings. Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99ATM are also contemplated to be suitable. Various commercially available $C_{16}$ isoparaffins, such as isohexadecane (having the tradename Permethyl®) are also suitable. Examples of preferred volatile hydrocarbons include polydecanes, such as isododecane and isodecane, including for example, Permethyl-99A (Presperse Inc.) and the $C_7$-$C_8$ through $C_{12}$-$C_{15}$ isoparaffins such as the Isopar Series, available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers include emulsifying waxes, emulsifying polyhydric alcohols, polyether polyols, polyethers, mono- or di-ester of polyols, ethylene glycol monostearates, glycerin mono-stearates, glycerin di-stearates, silicone-containing emulsifiers, soya sterols, fatty alcohols such as cetyl alcohol, acrylates, fatty acids such as stearic acid, fatty acid salts, and mixtures thereof. Some preferred emulsifiers include soya sterol, cetyl alcohol, stearic acid, emulsifying wax, acrylates, silicone containing emulsifiers, and mixtures thereof. Other specific emulsifiers that can be used with the compositions described herein include, but are not limited to, one or more of the following: $C_{10-30}$ alkyl acrylate crosspolymer; Dimethicone PEG-7 isostearate; acrylamide copolymer; mineral oil; sorbitan esters; polyglyceryl-3-diisostearate; sorbitan monostearate; sorbitan tristearate; sorbitan sesquioleate; sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference. These emulsifiers typically will be present in the composition in an amount from about 0.001% to about 10% by weight, in particular in an amount from about 0.01% to about 5% by weight, and more preferably, from about 0.1% to about 3% by weight. Based on the teachings herein, a person skilled in the art will be able to select a suitable emulsifier, or any other materials described herein, and/or in an amount thereof, such that one or more of the desired properties of the cosmetic compositions of the instant invention can be preserved.

The oil phase may comprise one or more volatile and/or non-volatile silicone oils. Volatile silicones include cyclic and linear volatile dimethylsiloxane silicones. In some embodiments, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from about 0.65 to about 600,000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones); GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)$_m$- and/or -(PO)$_n$- groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685, 952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone, dimethicone copolyol, dimethicone copolyol, caprylic/capric triglycerides, polyglyceryl-4 isostearate, cetyl dimethicone copolyol, hexyl laurate, dimethicone copolyol, cyclopentasiloxane, and any combination of two or more of these. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), dimethicone PEG-10/15 crosspolymer (trade name KSG-210, Shin-Etsu), and dimethicone PEG-7 isostearate. The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The compositions may include liposomes. The liposomes may comprise other additives or substances and/or may be modified to more specifically reach or remain at a site following administration. Additional suitable delivery vehicles include, e.g., niosomes, submicron emulsions, polymeric encapsulants, gels, creams, lotions, and combinations thereof.

The composition may optionally comprise other cosmetic actives and excipients, obvious to those skilled in the art including, but not limited to, fillers, emulsifying agents, surfactants, film formers, chelating agents, such as EDTA, gelling agents, thickeners, emollients, humectants, moisturizers, vitamins, minerals, viscosity and/or rheology modifiers, sunscreens, retinoids, hormonal compounds, alpha-hydroxy acids, alpha-keto acids, anti-mycobacterial agents, antifungal agents, antimicrobials, antivirals, analgesics, lipidic compounds, antineoplastics, immune system boosting agents, anti-allergenic agents, H1 or H2 antihistamines, anesthetics, antiseptics, insect repellents, skin cooling compounds, skin protectants, skin penetration enhancers, exfollients, lubricants, fragrances, colorants, hypopigmenting agents, preservatives (e.g., DMDM Hydantoin/Iodopropynylbutylcarbonate), stabilizers, pharmaceutical agents, photostabilizing agents, neutralizers (e.g., triethanolamine), and mixtures thereof. In addition to the foregoing, the cosmetic compositions of the invention may contain any other compound for the treatment of skin conditions or disorders. Based on the teachings herein, a person skilled in the art will be able to select any of these or other materials, and/or in an amount thereof, such that one or more of the desired properties of the cosmetic compositions of the instant invention can be preserved.

Preservatives may include, for example, alcohols, glycols, parabens, quaternary nitrogen-containing compounds, isothiazolinones, aldehyde-releasing agents, antioxidants, halogenated compounds, and combinations thereof. Illustrative alcohols include, e.g., phenoxyethanol, isopropyl alcohol, and benzyl alcohol; illustrative glycols include, e.g., propylene, butylene, and pentylene glycol; illustrative parabens (also known as parahydroxybenzoic acids) include, e.g., methyl, propyl and butyl-parabens; illustrative quaternary nitrogen-containing compounds include, e.g., benzalkonium chloride and Quaternium 15; illustrative isothiazolinones include, e.g., methylisothiazolinone and methylchloroisothiazolinone; illustrative aldehyde-releasing agents include, e.g., DMDM hydantoin, imidazolidinyl urea, and diazolidinyl urea; illustrative antioxidants include, e.g., butylated hydroxytoluen and tocopherol, and illustrative halogenated compounds include, e.g., triclosan and chlorohexidine digluconate. Additional examples of preservatives useful for the purposes of the present invention can be found, for example, in Steinberg, D. "Frequency of Use of Preservatives 2001" Cosmet. Toilet. 117, 41-44, (2002) and, "Preservative Encyclopedia" Cosmet. Toilet. 117, 80-96 (2002).

Colorants may include, for example, organic and inorganic pigments and pearlescent agents. Suitable inorganic pigments include, but are not limited to, titanium oxide, titanium dioxide, zirconium oxide, and cerium oxide, as well as zinc oxide, iron oxide, chromium oxide, and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning), and silicone resin microbeads (Tospearl™ from Toshiba), and the like.

In some preferred embodiments, the compositions include at least one other skin (or hair) lightener, at least one other anti-inflammatory agent, at least one other anti-lipid agent; at least one other exfoliating agent, and/or at least one other anti-aging agent. Other conventional additives include: vitamin derivatives such as ascorbyl monopalmitate; thickeners such as hydroxyalkyl cellulose; gelling agents; and structuring agents such as bentonite, smectite, magnesium aluminum silicate and lithium magnesium silicate. In some embodiments of the invention, the topical compositions of the present invention may also include one or more of the following: an emollient, an optical diffuser, a sunscreen, and an antioxidant. These additives may also act as anti-aging agents. Based on the teachings herein, a person skilled in the art will be able to select suitable emollients, optical diffusers, sunscreens, and/or antioxidants, or any other materials, and/or in an amount thereof, such that one or more of the desired properties of the cosmetic compositions of the instant invention can be preserved.

An emollient provides the functional benefits of enhancing skin smoothness and reducing the appearance of fine lines and coarse wrinkles Examples include isopropyl myristate, petrolatum, isopropyl lanolate, silicones (e.g., methicone, dimethicone), oils, mineral oils, fatty acid esters, cetyl ethylhexanoate, $C_{12-15}$ alkyl benzoate, isopropyl isostearate, diisopropyl dimer dillinoeate, or any mixtures thereof. The emollient may be preferably present from about 0.1 wt % to about 50 wt % of the total weight of the composition.

An optical diffuser is a particle that changes the surface optometrics of skin, resulting in a visual blurring and softening of, for example, lines and wrinkles Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 weight % to about 20 weight % of the total weight of the composition.

A sunscreen for protecting the skin from damaging ultraviolet rays may also be included. Preferred sunscreens are those with a broad range of UVB and UVA protection, such as ocrocrylene, avobenzone (Parsel 1789), octyl methoxycinnamate, octyl salicylate, oxybenzone, homosylate, benzophenone, camphor derivatives, zinc oxide, and titanium dioxide. When present, the sunscreen may comprise from about 0.01 weight % to about 70 weight % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate and sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 weight % to about 10 weight %, and more preferably from about 0.01 weight % to about 5 weight %, of the total weight of the composition.

EXAMPLES

Example 1

Decrease in Melanin Synthesis by Inhibiting Calcium Influx

Modified yeast peptide fractions comprising a zinc-complexed peptide comprising SEQ ID NO:1 were tested in vitro for the ability to inhibit calcium influx into pigment-producing cells. An experiment was designed to measure intracellular calcium in B16 melanoma cells using Fluo-4 NW Calcium Assay Kits (Invitrogen) as per manufacturer's instructions. B16 mouse melanoma cell lines (ATCC, cat. #: CRL-6475) were grown in 96-well tissue culture treated dishes in growth medium. Prior to calcium treatment, growth medium from the B16 cell cultures was removed and 100 µL of the dye loading solution was added quickly to each well of a 96-well plate. Plates were incubated at 37° C. for 30 minutes, then at room temperature for an additional 30 minutes. Dye buffer was removed and plates were washed once with 1×PBS and replaced with an assay buffer that contains calcium (and was formed according to the manufacturer's directions) along with a test compound. The test compounds used were: 100 µM 2-APB, a known calcium influx inhibitor, and modified yeast peptide fractions comprising different concentrations of zinc-complexed peptide comprising SEQ ID NO:1, including 0.1% zinc-complexed peptide. The vehicle (assay buffer without a test compound) was used as a control.

Fluorescence was measured using a micro-plate reader at excitation/emission wavelengths of 485 nm/530 nm, respectively. The reader was set to read florescence every 30 seconds for a period of 5 minutes. At the end of 5 minutes, calcium ion influx was stimulated by the addition of Thapsigargin to the assay buffer, to give a final concentration of 1 µM in each well. Assay buffer without Thapsigargin was used as a negative control. The fluorescence micro-plate reader was set to take fluorescence measurements every 30 seconds for a period of 30 minutes, again at excitation/emission wavelengths of 485 nm/530 nm, respectively. The florescence units were plotted against time (in minutes) to give a calcium influx graph. The effect of 2APB or modified peptide fraction versus the control was compared using the area under the curve of the calcium influx peak.

It was observed that 100 µM 2-APB treatment inhibited calcium entry into the cells by 86%. Furthermore, it was unexpectedly observed that treatment of B16 pigment cells with modified peptide fraction comprising 0.1% zinc-complexed peptide comprising SEQ ID NO:1 also inhibited calcium entry into the cells, and did so by about 45%.

Next, the effects of 2-APB and modified peptide fractions having a zinc-complexed peptide comprising SEQ ID NO:1 on melanin synthesis were examined in B16 cells. B16 mouse melanoma cell lines (ATCC, cat. #: CRL-6475) were grown in 96-well tissue culture treated dishes (Falcon) and treated with a test compound to determine its ability to modulate pigment formation (melanin synthesis). Specifically, cells were exposed to 100 µM 2-APB or modified yeast peptide fractions comprising different concentrations of zinc-complexed peptide comprising SEQ ID NO:1, including 1% and 0.1% zinc-complexed peptide, for seven (7) days. Following the treatment period, the level of melanin synthesized was quantified using a Packard micro-plate reader at 540 nm.

After quantifying the amount of melanin synthesized, cell viability was determined using the MTT conversion method. The MTT conversion method measures the reduction of MTT dye from a yellow, water-soluble, tetrazolium salt to a bluish-purple insoluble formazan precipatate by NAD(P)H-dependent microsomal dehydrogenase enzymes, which only function in viable cells. The intensity of blue color is thus indicative of cell viability. After melanin synthesis quantification, the cultures were exposed to MTT dye solution with a concentration of 1 mg/ml for three hours. Formazan material was solubilized with reagent alcohol (95% ethanol: 5% isopropanol) and shaken on an orbital shaker for 15 minutes. MTT dye uptake and conversion by viable cells was determined by measuring the extracted formazan at 570 nm using a Packard micro-plate reader.

After normalizing to cell viability, total pigmentation then was calculated, and expressed as a percent activity of control. It was surprisingly observed that 2-APB inhibited melanin synthesis by 77%; and the 0.1% and 1% zinc-complexed peptide exhibited inhibitory effects of 27% and 52%, respectively, relative to control (p<0.05). The results suggest that compositions comprising modified yeast peptide fractions comprising a metal-complexed peptide comprising SEQ ID NO:1 and/or other calcium influx inhibitors, can be used to reduce hyper-pigmentation, for example, when topically applied to hyper-pigmented skin.

Example 2

Decrease in TNFa Production by Modified Yeast Peptide Fractions

Modified yeast peptide fractions comprising a zinc-complexed peptide comprising SEQ ID NO:1 were tested in vitro for the ability to decrease TNFa production, which is known to be involved in inflammation. Human Epidermal Keratinocyte cells were cultured in growth medium in 6-well plates at 37° C. and 5% $CO_2$ for 48 hours. Cells were treated with 1 mL of growth medium containing 10 ng/mL of phorbol myristyl acetate (PMA) to stimulate Tumor Necrosis Factor alpha (TNFa). Cells were also co-treated with modified yeast peptide fractions comprising different concentrations of zinc-complexed peptide comprising SEQ ID NO:1, including 0.1% and 1% zinc-complexed peptide.

After 6 hours of incubation at 37° C., culture medium was collected and analyzed for levels of TNFa using an ELISA kit (Quantikine Human TNF-α/TNFSF1A, R&D Systems). It was observed that treatment with the modified peptide fractions comprising 0.1% and 1% zinc-complexed peptide comprising SEQ ID NO:1 inhibited the induction of TNFa by PMA by 25% and 46%, respectively (p<0.05). The results suggest that topical application of compositions comprising modified yeast peptide fractions comprising a metal-complexed peptide comprising SEQ ID NO:1 can reduce inflammation and result in improvements of symptoms associated with inflammatory skin conditions.

Example 3

Decrease in PPAR-γ Expression by Modified Yeast Peptide Fractions

Modified yeast peptide fractions comprising a zinc-complexed peptide comprising SEQ ID NO:1 were tested in vitro for the ability to decrease PPAR-γ expression, which is known to be involved in lipid production and storage. PPAR-γ gene expression was monitored using a luciferase reporter assay system. This assay system involves the PPAR-γ promoter sequence linked to the luciferase enzyme coding region. The level of luciferase activity is indicative of gene expression activity from the PPAR-γ promoter. The PPAR-γ reporter was constructed by inserting three copies of PPAR element [(ACO)3] into the pGL3 vector. The constructs then were transfected into CV-1 cells.

CV-1 cells were plated in 24-well plates at a density of 60% in DMEM media supplemented with 10% fetal calf serum (delipided). After reaching 85% confluence, cells were transfected using a transfection mixture with LipofectAMINE and Plus Reagent. The transfection mixture contained the PPAR-γ reporter (ACO3-tk) construct (100 ng/well), as well as PPAR-γ plasmid (100 ng/well) and a reference plasmid pRL-NULL (10 ng/well). The plasmid constructs were initially mixed with 20 µl Plus Reagent, diluted in 750 µl serum and antibiotic-free medium for 15 minutes at RT, and then mixed with 30 µl LipofectAMINE Reagent, diluted in 5 ml of the same medium, for an additional 15 minutes. The final transfection complexes (1.5 ml/per well) were added to a monolayer of CV-1 cells. After a 3 hour-incubation, the media was replaced by normal culture medium and incubated overnight in a 37° C. humidified incubator with 5.0% $CO_2$.

The transfected cells were treated with modified yeast peptide fractions comprising different concentrations of zinc-complexed peptide comprising SEQ ID NO:1, including a composition comprising 0.004% zinc-complexed peptide. As a positive control, cells were treated with ciglitazone at 10 µM; as a negative control, cells were treated with the vehicle without any stressed yeast extract. The treated cells were cultured for an additional 24 hours, washed once with phosphate buffered saline, and lysed in 100 µl cell lysis buffer by gently shaking for 30 minutes at room temperature. Cell lysates were collected by scraping after a 3 hour-incubation at −80° C. All experiments were conducted in triplicate and proper positive or negative controls included.

Luciferase activity was determined with a Dual-Luciferase Reporter Assay System (Promega) as described by the manufacturer. This system contained two substrates, used to determine the activity of two luciferases sequentially. Firefly luciferase activity, which represented the reporter gene activity, was initiated by mixing an aliquot of lysate (10 µl) with Luciferase Assay Reagent II. Then the firefly luminescence was quenched and *Renilla* luminescence was simultaneously activated by adding Stop & Glo Reagent to the sample plate. The ratio of the firefly luminescence signal over *Renilla* luminescence signal in each sample was calculated, and the signal ratios from extract-treated wells to that from vehicle-treated wells were recorded as a fold of induction (>1) or suppression (<1).

In triplicate tests, the addition of a modified peptide fraction comprising 0.004% zinc-complexed peptide comprising SEQ ID NO:1 was found to decrease expression of the reporter gene by 30% (p<0.05), indicating a 30% decrease in PPAR-γ expression. The results suggest that topical application of compositions comprising modified yeast peptide fractions comprising a metal-complexed peptide comprising SEQ ID NO:1 can control lipid production, for example reducing sebum overproduction and/or cellulite.

Example 4

Increase in Collagen Synthesis by Modified Yeast Peptide Fractions

Modified yeast peptide fractions comprising a zinc-complexed peptide comprising SEQ ID NO:1 were tested in vitro for the ability to increase synthesis of collagen, specifically, dermal matrix component procollagen I, which is known to be reduced in aging skin. Human dermal fibroblasts (Cascade Biologics) were cultured in 96-well tissue culture plates in 200 W growth medium (DMEM, 5% FBS, 1% L-Glut, and 1% antibiotics) and incubated for 24 hours at 37° C. Cells were treated with modified yeast peptide fractions comprising different concentrations of zinc-complexed peptide comprising SEQ ID NO:1 diluted in growth medium, including fractions comprising 0.1% zinc-complexed peptide diluted in growth medium, and incubated for 72 hours at 37° C. After this time period, conditioned media was collected and assayed for the levels of procollagen I, a precursor form of collagen I, as discussed herein.

Procollagen I was measured using a solid-phase sandwich ELISA immunoassay (Procollagen Type-I C-Peptide EIA Kit) purchased from Takara Bio USA, WI, USA, following the manufacturer's instructions. A modified yeast peptide fraction comprising 0.1% zinc-complexed peptide comprising SEQ ID NO:1 stimulated procollagen I by 20.5%. The results suggest that topical application of compositions comprising modified yeast peptide fractions comprising a metal-complexed peptide comprising SEQ ID NO:1 can increase collagen synthesis and thus collagen levels in the skin, thereby forestalling and/or improving unwanted signs of skin aging.

Example 5

Decrease in Collagenase Activity by Modified Yeast Peptide Fractions

Modified yeast peptide fractions comprising a zinc-complexed peptide comprising SEQ ID NO:1 were tested in vitro for the ability to decrease metalloproteinase activity. Specifically, Enzcheck Gelatinase/Collagenase Assay Kit (E-12055) made by Molecular Probes was used. This assay uses a DQ gelatin substrate that has been labeled with Molecular Probes BODIPY FL dye such that the conjugate's fluorescence has been quenched. Upon digestion of the collagen substrate, fluorescence is revealed. The collagenase used in this assay was metalloproteinase purified from *Clostridium histolyticum*.

Modified yeast peptide fractions comprising different concentrations of zinc-complexed peptide comprising SEQ ID NO:1, including 1% zinc-complexed peptide, were applied to this assay to determine their ability to inhibit the metalloproteinase from digesting the DQ gelatin substrate. A decrease in fluorescent emission from the reaction mixture is indicative of inhibition. Reactions were incubated in the dark at room temperature for one hour. Readings were taken using a fluorescence micro-plate reader at the excitation/emission wavelengths of 485 nm/530 nm, respectively.

It was observed that the modified peptide fractions comprising 1% zinc-complexed peptide comprising SEQ ID NO:1 decreased metalloproteinase activity by 20%. The results suggest that topical application of compositions comprising modified yeast peptide fractions comprising a metal-complexed peptide comprising SEQ ID NO:1 can decrease metalloproteinase activity, thereby reducing loss of collagen and associated unwanted features of skin aging, e.g., by reducing loss of skin firmness and plumpness.

Example 6

Increase in Hyaluronic Acid by Modified Yeast Peptide Fractions

Modified yeast peptide fractions comprising a zinc-complexed peptide comprising SEQ ID NO:1 were tested in vitro for the ability to increase hyaluronic acid production, specifically in dermal fibroblasts. Human dermal fibroblasts (Cascade Biologics) were cultured in 96-well tissue culture plates in 200 μl growth medium (DMEM, 5% FBS, 1% L-Glut, and 1% antibiotics) and incubated for 24 hours at 37° C. Cells treated with modified yeast peptide fractions comprising different concentrations of zinc-complexed peptide comprising SEQ ID NO:1 diluted in growth medium, including fractions comprising 0.01% zinc-complexed peptide diluted in growth medium, and incubated for 24 hours at 37° C. After this time period, conditioned media was collected and assayed for the levels of hyaluronic acid, using an assay kit purchased from Corgenix, Inc., CO, USA, following the manufacturer's instructions.

It was observed that modified peptide fractions comprising 0.01% zinc-complexed peptide comprising SEQ ID NO:1 stimulated hyaluronic acid synthesis by 100%. The results suggest that topical application of compositions comprising a modified yeast peptide fractions comprising a metal-complexed peptide comprising SEQ ID NO:1 can increase hyaluronic acid production, thereby reducing one or more of the unwanted features associated with skin aging, e.g., by improving skin hydration and resiliency.

Example 7

Increase in Kallikreins Activity by Modified Yeast Peptide Fractions

Modified yeast peptide fractions comprising a zinc-complexed peptide comprising SEQ ID NO:1 were tested in vitro for the ability to increase enzymatic activity of a member of the KLK family, specifically, recombinant human (rh) KLK5. Recombinant human KLK5 (R&D Systems; Cat No. 1108-SE) was pre-incubated with modified yeast peptide fractions comprising different concentrations of zinc-complexed peptide comprising SEQ ID NO:1, including 0.1%, 0.01%, and 0.001% zinc-complexed peptide. Following pre-treatment, KLK5 activity was assessed by measuring the rate of peptide bond cleavage of a synthetic substrate. The substrate was conjugated to a quenched fluorescent group (Boc-V-P-R-AMC Fluorogenic Peptide Substrate, R&D Systems, Cat No. ES011), so that upon cleavage of the adjacent peptide bond, the fluorescence is revealed, resulting in a measureable emission at a wavelength of 612 nm when excited at a wavelength of 340 nm. An increase in the fluorescence reading indicates increased rhKLK5 activity.

It was observed that modified peptide fractions comprising 0.1%, 0.01%, and 0.001% zinc-complexed peptide comprising SEQ ID NO:1 stimulated KLK5 activity by 23%, 27% and 31% respectively, surprisingly giving an inverse dose-response. The results suggest that topical application of compositions comprising modified yeast peptide fractions comprising a metal-complexed peptide comprising SEQ ID NO:1 can increase KLKs activity, thereby enhancing exfoliation and reducing one or more unwanted features associated with skin aging, e.g., by improving skin luster and/or brightness.

Example 8

Skin Lightening and/or Anti-Aging Essence Formulation

Exemplary cosmetic compositions comprising modified yeast peptide fractions comprising a zinc-complexed peptide comprising SEQ ID NO:1 for topical application to the skin are provided below. The compositions are provided in the form of an essence that finds use in anti-aging and/or skin lightening applications.

| | |
|---|---|
| Water | qs |
| Glycerin | 2-10% |
| Pentylene Glycol | 2-5% |
| Disodium EDTA | 0.2% |
| Sodium polyacrylate | 0.2-2% |
| Silica | 0.2-2% |
| $Zn^{2+}$-complexed peptide | 0.001-2% |
| Phenoxyethanol | 0.1-1% |

Example 9

Skin Lightening and/or Anti-Aging Essence Formulation

Further exemplary cosmetic compositions comprising modified yeast peptide fractions comprising a zinc-complexed peptide comprising SEQ ID NO:1 for topical application to the skin are provided below. The compositions again are provided in the form of an essence that finds use in anti-aging and/or skin lightening applications.

| | |
|---|---|
| Water | qs |
| Glycerin | 2-10% |
| Pentylene Glycol | 2-5% |
| Disodium EDTA | 0.2% |
| Xanthan gum | 0.2-2% |
| Silica | 0.2-2% |
| $Zn^{2+}$-complexed peptide | 0.001-2% |
| Ascorbyl Glucoside | 0.001-2% |
| Phenoxyethanol | 0.1-1% |

Example 10

Skin Lightening and/or Anti-Aging Cream Formulation

Exemplary cosmetic compositions comprising modified yeast peptide fractions comprising a zinc-complexed peptide comprising SEQ ID NO:1 for topical application to the skin are provided below. The compositions are provided in the form of a cream that finds use in anti-aging and/or skin lightening applications.

| | |
|---|---|
| Water | qs |
| Glycerin | 2-10% |
| Disodium EDTA | 0.2% |
| $Zn^{2+}$-complexed peptide | 0.001-2% |
| Ascorbyl Glucoside | 0.001-2% |
| Tetrahecyldecyl ascorbate | 0.00001-2% |
| Carrot Root extract | 0.001-2% |
| Soybean seed extract | 0.001-1% |
| Carbopol | 0.1-2% |
| Lecithin hydrogenated | 0.1-1% |
| Cetyl Caprylate | 2-15% |
| Phenoxyethanol | 0.1-1% |

Example 11

Skin Lightening and/or Anti-Aging SPF 20 Day Cream Formulation

Exemplary cosmetic compositions comprising modified yeast peptide fractions comprising a zinc-complexed peptide comprising SEQ ID NO:1 for topical application to the skin are provided below. The compositions are provided in the form of a daytime cream that finds use in anti-aging and/or skin lightening applications, and further provides SPF 20.

| | |
|---|---|
| Water | qs |
| Glycerin | 2-10% |
| Disodium EDTA | 0.2% |
| $Zn^{2+}$-complexed peptide | 0.001-2% |
| Ascorbyl Glucoside | 0.001-2% |
| Tetrahecyldecyl ascorbate | 0.00001-2% |
| Carrot Root extract | 0.001-2% |
| Soybean seed extract | 0.001-1% |
| Carbopol | 0.1-2% |
| Cetearyl glucoside | 0.5-3% |
| Ethylhexyl methoxycinnamate | 5-10% |
| Benzophenone-3 | 1-5% |
| Octyl Salicylate | 3-5% |
| Butyl Methoxydibenzoylmethane | 1-5% |
| Phenoxyethanol | 0.1-1% |

Example 12

Exfoliating Foaming Cleanser Formulation

Exemplary cosmetic compositions comprising modified yeast peptide fractions comprising a zinc-complexed peptide comprising SEQ ID NO:1 for topical application to the skin are provided below. The compositions are provided in the form of a foaming cleanser that further acts to enhance exfoliation during cleansing.

| | |
|---|---|
| Water | qs |
| Stearic acid | 15-35% |
| Potassium Hydroxide | 4-8% |
| $Zn^{2+}$-complexed peptide | 0.001-2% |
| Phenoxyethanol | 0.1-1% |

Example 13

Skin Lightening and/or Anti-Aging Essence Formulation

Exemplary cosmetic compositions comprising modified yeast peptide fractions comprising a complexed peptide comprising SEQ ID NO:1 for topical application to the skin are provided below. The compositions are provided in the form of an essence that finds use in anti-aging and/or skin lightening applications.

| | |
|---|---|
| Water | qs |
| Glycerin | 2-10% |
| Humectant | 2-5% |
| Chelating agent | 0.2% |
| Thickener | 0.2-2% |
| Silica | 0.2-2% |
| Complexed peptide | 0.001-2% |
| Preservative | 0.1-1% |

Various formulations are prepared according this formula where the peptide is complexed with calcium ($Ca^{2+}$), copper ($Cu^{2+}$), magnesium ($Mg^{2+}$), manganese ($Mn^{2+}$), nickel ($Ni^{2+}$), and iron ($Fe^{2+}$). Each formulation is topically applied to skin in need of depigmenting, including skin affected by hyper-pigmentation.

Example 14

UV-Stressed Yeast Lysates Failed to Decrease in Melanin Synthesis

UV-stressed yeast extract failed to demonstrate any significant reduction of melanin synthesis. Comparative tests for decreasing melanin synthesis in pigment cells were conducted for the UV-stressed yeast extracts described in U.S. Pat. No. 5,643,587 and the modified yeast peptide fractions of the instant invention. When pigment cells were exposed to the UV-stressed yeast extract, at concentrations of 0.1%, 0.01% and 0.001%, melanin levels changed by +2%, −6% and −8%. These results indicate that this yeast extract does not possess the ability to modulate melanin levels in this system.

On the other hand, when pigment cells were exposed to modified yeast peptide fractions comprising 1% and 0.1% zinc-complexed peptide comprising SEQ ID NO:1 of the instant invention, there was an appreciable reduction in melanin synthesis under the same test conditions. As reported in Example 1 above, the 0.1% and 1% zinc-complexed peptide composition inhibited melanin synthesis by 27% and 52%, respectively. The results indicate the surprising lightening benefits of the inventive compositions compared with UV-stressed yeast extracts of the prior art, in particular the melanin synthesis-decreasing abilities of modified yeast peptide fractions of UV-stressed yeast extracts containing a peptide comprising SEQ ID NO:1 as the dominant fraction and complexed with zinc ions.

The terms used herein have their ordinary and accustomed meanings in the art, unless otherwise specified. All weights percentages referred to herein are given in terms of "% by weight" or "weight %" of the total composition, which refers to the weight percent of the total formulation after addition of any carriers, solvents, emollients, or other components before application to the skin (or hair), unless otherwise indicated.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for treating hyper-pigmentation comprising topically applying to an area of hyper-pigmented skin a composition comprising an effective amount of a peptide comprising SEQ ID NO:1, or a homolog thereof having one or more conservative amino acid substitutions, in a cosmetically acceptable vehicle,
   wherein said peptide or homolog thereof has been modified by complexation with one or more metal ions, and
   wherein said metal-complexed peptide is present in an amount sufficient to decrease melanin synthesis in said area of hyper-pigmented skin.

2. The method according to claim 1, wherein said peptide is a modified yeast peptide fraction comprising a peptide fraction of a yeast extract.

3. The method according to claim 1, wherein said composition further includes a calcium influx inhibitor selected from the group consisting of 2-aminoethyl diphenylborate; Aminohexahydrofluorene; Bepridil, Calcicludine; Calciseptine; Calmidazolium chloride; Nifedipine; Verapamil; FS2 (Dendroaspis polylepis polylepis); Galanin; Protopine; Tetrahydropalmatine; Somatostatin-14; L-Stepholidinealverine; Manganese; Magnesium; and salts thereof.

4. The method according to claim 1, wherein said composition further includes at least one other skin lightener, selected from thiodipropionic acid (TDPA) or an ester derivative thereof.

5. A method for lightening skin or hair, comprising topically applying to said skin or hair a composition comprising an effective amount of a peptide comprising SEQ ID NO:1, or a homolog thereof having one or more conservative amino acid substitutions, in a cosmetically acceptable vehicle
   wherein said metal-complexed peptide or homolog thereof has been modified by complexation with one or more metal ions and
   wherein said metal-complexed peptide is applied for a time sufficient to lighten said skin or hair.

6. A method for providing a benefit to human skin comprising topically applying to skin in need thereof a composition comprising an effective amount of a peptide comprising SEQ ID NO:1, or a homolog thereof having one or more conservative amino acid substitutions, in a cosmetically acceptable vehicle, wherein said peptide or homolog thereof has been modified by complexation with one or more metal ions.

7. The method according to claim 6, wherein said metal ion is a divalent metal ion selected from one or more of calcium, cadmium, cobalt, copper, magnesium, manganese, nickel, beryllium, strontium, iron, mercury, and zinc ions.

8. The method according to claim 6, wherein said metal-complexed peptide or homolog thereof is present in an amount sufficient to decrease at least one of melanin synthesis; TNFa production; PPARs signaling; and metalloproteinase activity; and/or to increase at least one of KLKs activity; hyaluronic acid production; and collagen synthesis.

9. The method according to claim 6, wherein said skin benefit is selected from the group consisting of: (a) treatment of prevention of a sign of skin aging; (b) treatment and/or prevention of fine lines or wrinkles; (c) reduction of skin pore size; (d) improvement in skin thickness, plumpness, and/or tautness; (e) improvement in skin suppleness and/or softness; (f) improvement in skin tone, radiance, and/or clarity; (g) improvement in skin texture and/or promotion of retexturization; (h) improvement in skin barrier repair and/or function; (i) improvement in appearance of skin contours; (j) restoration of skin luster and/or brightness; (k) replenishment of essential nutrients and/or constituents in the skin; (l) improvement of skin appearance decreased by menopause; (m) improvement in skin moisturization and/or hydration; (n) increase in and/or preventing loss of skin elasticity and/or resiliency; (o) improvement in procollagen and/or collagen synthesis; (p) treatment and/or prevention of skin sagging or atrophy; (q) enhancing exfoliation and/or reducing dryness; (r) treatment and/or prevention of skin hyper-pigmentation; (s) treatment and/or prevention of inflammation; (t) treatment and/or prevention of excess sebum output; and (u) treatment and/or prevention of cellulite.

10. The method according to claim 9, wherein said skin hyper-pigmentation comprises an age spot, a mottled area, a discrete hyper-pigmented area, a tanned area, an under-arm area, or a melasmic patch.

11. The method according to claim 9, wherein said inflammation comprises an acne lesion, a pimple, or an irritated area.

12. A method for treating inflammation of skin, comprising topically applying to said skin a composition comprising an effective amount of a peptide comprising SEQ ID NO:1, or a homolog thereof having one or more conservative amino acid substitutions, in a cosmetically acceptable vehicle for a time sufficient to eradicate, reduce, ameliorate; or reverse one or more unwanted features associated with inflammation, wherein said peptide or homolog thereof has been modified by complexation with one or more metal ions.

13. A topical composition comprising: from 0.001 weight % to 5 weight % of peptide comprising SEQ ID NO:1, or a homolog thereof having one or more conservative amino acid substitutions, in a cosmetically acceptable vehicle; wherein said metal-complexed peptide or homolog thereof has been modified by complexation with one or more metal ions; and wherein said topical composition is in the form of a lotion, cream, essence ointment, gel, or stick.

14. A method for treating skin lipid over-production comprising topically applying to an area of skin affected by lipid over-production a composition comprising an effective amount of a peptide comprising SEQ ID NO:1, or a homolog thereof having one or more conservative amino acid substitutions, in a cosmetically acceptable vehicle for a time sufficient to reduce said lipid over-production, wherein said peptide or homolog thereof has been modified to be in complexation with a metal ion.

15. A method for enhancing exfoliation comprising topically applying to an area of skin in need thereof a composition comprising an effective amount of a metal-complexed peptide comprising SEQ ID NO:1, or a homolog thereof having one or more conservative amino acid substitutions, in a cosmetically acceptable vehicle; and rubbing said composition against said skin to enhance exfoliation; wherein said metal-complexed peptide or homolog thereof has been modified by complexation with one or more metal ions.

16. The method according to claim 1, wherein said metal-complexed peptide consists essentially of SEQ ID NO:1 in complexation with said metal ion.

17. The method according to claim 1, wherein said metal-complexed peptide is a chemically synthesized or recombinantly produced peptide modified to be in complexation with said metal ion.

18. The method according to claim 1, wherein said metal ion is a divalent metal ion selected from one or more of calcium, cadmium, cobalt, copper, magnesium, manganese, nickel, beryllium, strontium, iron, mercury, and zinc ions.

19. The method according to claim 1, wherein said metal ion is zinc ion.

20. The topical composition according to claim 13, wherein said metal-complexed peptide consists essentially of SEQ ID NO:1 in complexation with said metal ion.

21. The topical composition according to claim 13, wherein said metal-complexed peptide is a modified yeast peptide fraction comprising a peptide fraction of a yeast extract, wherein said peptide fraction has been modified to be in complexation with said metal ion.

22. The topical composition according to claim 13, wherein said metal-complexed peptide is a chemically synthesized or recombinantly produced peptide modified to be in complexation with said metal ion.

23. The topical composition according to claim 13, wherein said metal ion is a divalent metal ion selected from one or more of calcium, cadmium, cobalt, copper, magnesium, manganese, nickel, beryllium, strontium, iron, mercury, and zinc ions.

24. The topical composition according to claim 13, wherein said metal ion is zinc ion.

* * * * *